US008889133B2

(12) United States Patent
Skokos

(10) Patent No.: US 8,889,133 B2
(45) Date of Patent: Nov. 18, 2014

(54) METHODS OF TREATING DIABETES WITH DLL4 ANTAGONISTS

(75) Inventor: Dimitris Skokos, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 449 days.

(21) Appl. No.: 13/015,652

(22) Filed: Jan. 28, 2011

(65) Prior Publication Data

US 2011/0189176 A1 Aug. 4, 2011

Related U.S. Application Data

(60) Provisional application No. 61/299,801, filed on Jan. 29, 2010, provisional application No. 61/361,687, filed on Jul. 6, 2010, provisional application No. 61/388,697, filed on Oct. 1, 2010.

(51) Int. Cl.
*A61K 39/395* (2006.01)
*A61P 3/10* (2006.01)
*C07K 16/28* (2006.01)
*A61K 38/16* (2006.01)
*A61K 39/00* (2006.01)

(52) U.S. Cl.
CPC ........... *C07K 16/28* (2013.01); *A61K 2039/505* (2013.01); *C07K 2317/73* (2013.01)
USPC ........ 424/133.1; 424/143.1; 514/6.9; 514/7.3

(58) Field of Classification Search
CPC ............... C07K 16/28; C07K 2317/73; A61K 2039/505
USPC ........................ 424/133.1, 143.1; 514/6.9, 7.3
See application file for complete search history.

(56) References Cited

U.S. PATENT DOCUMENTS

| 2006/0134121 A1 | 6/2006 | Thurston et al. |
| 2008/0107648 A1 | 5/2008 | Noguera et al. |
| 2008/0181899 A1 | 7/2008 | Papadopoulos et al. |
| 2011/0189200 A1 | 8/2011 | Skokos |

FOREIGN PATENT DOCUMENTS

| WO | 2007070671 A2 | 6/2007 |
| WO | 2007143689 A2 | 12/2007 |
| WO | 2008019144 A2 | 2/2008 |
| WO | 2008042236 A2 | 4/2008 |
| WO | 2008076379 A2 | 6/2008 |
| WO | 2011/025964 A2 | 3/2011 |
| WO | WO 2011/094465 A1 | 8/2011 |
| WO | WO 2011/094467 A2 | 8/2011 |

OTHER PUBLICATIONS

Billiard et al. J Exp Med. May 7, 2012;209(5):1011-28. doi: 10.1084/jem.20111615. Epub Apr. 30, 2012. (Abstract).*

Jurynczyk M., et al. "Overcoming failure to repair demyelination in EAE: gamma-secretase inhibition of Notch signaling." Journal of the Neurological Sciences. 2008. 265(1-2): 5-11. (Available online Oct. 18, 2007).
Jurynczyk M., et al. "Notch3 inhibition in myelin-reactive T cells down-regulates protein kinase C theta and attenuates experimental autoimmune encephalomyelitis." Journal of Immunology. 2008. 180(4): 2634-2640.
Takeichi N., et al. "Ameliorating effects of anti-Dll4 mAb on Theiler's murine encephalomyelitis virus-induced demyelinating disease." International Immunology. 2010. 22(9): 729-738.
Kim W., et al. "Notch signaling in pancreatic endocrine cell and diabetes." Biochemical and Biophysical Research Communications. 2010. 392(3): 247-521.
Amsen, D., et al. "Instruction of Distinct CD4 T Helper Cell Fates by Different Notch Ligands on Antigen-Presenting Cells." Cell (2004) 117:515-526.
Artavantis-Tsakonas, S., et al. "Notch Signaling: Cell Fate Control and Signal Integration in Development." Science (1999) 284: 770-776.
Darrasse-Jeze, G., et al. "Feedback control of regulatory T cell homeostasis by dendritic cells in vivo." Journal of Experimental Medicine (2009) 206(9): 1853-1862.
Di Santo, J.P. "A Guardian of T Cell Fate." Science (2010) 329: 44-45.
Fancke, B., et al. "M-CSF: a novel plasmacytoid and conventional dendritic cell poietin." Blood (2008) 111(1): 150-159.
Feyerabend, T.B., et al. "Deletion of Notch1 Converts Pro-T Cells to Dendritic Cells and Promotes Thymic B Cells by Cell-Extrinsic and Cell-Intrinsic Mechanisms." Immunity (2009) 30: 67-79.
Hozumi, K., et al. "Delta-like 4 is indispensable in thymic environment specific for T cell development." Journal of Experimental Medicine (2008) 205(11): 2507-2513.
Koch, U., et al. "Delta-like 4 is the essential, nonredundant ligand for Notch1 during thymic T cell lineage commitment." Journal of Experimental Medicine (2008) 205(11): 2515-2523.
Liu, K., et al. "In Vivo Analysis of Dendritic Cell Development and Homeostasis." Science (2009) 324: 392-397.
McGeachy, M.J., et al. "Natural Recovery and Protection from Autoimmune Encephalomyelitis: Contribution of CD4+CD25- Regulatory Cells within the Central Nervous System." Journal of Immunology (2005) 175(5): 3025-3032.

(Continued)

*Primary Examiner* — Lynn Bristol
(74) *Attorney, Agent, or Firm* — Alston & Bird LLP; Christopher Westberg

(57) ABSTRACT

The present invention provides methods of preventing, treating or ameliorating diabetes by administering to a subject in need thereof a therapeutically effective amount of Dll4 antagonists that block Dll4-Notch signal pathways. As observed in a mouse model of diabetes, Dll4 antagonists exhibit protective effects on pancreatic islets, lower blood glucose levels, and block the production of auto-antibodies, including those against insulin and glutamic acid decarboxylase 65 (GAD65), via the expansion of regulatory T cells (Tregs). Thus, the present invention further provides methods of lowering the levels of blood glucose, and/or reducing or blocking the production of auto-antibodies, by administering to a subject in need thereof a therapeutically effective amount of Dll4 antagonists. Suitable Dll4 antagonists for the invention include antibodies or antibody fragments that specifically bind Dll4 and block Dll4-Notch interactions, the extracellular domain of Dll4, and the like.

6 Claims, 20 Drawing Sheets

(56) References Cited

OTHER PUBLICATIONS

Merad, M., et al. "Dendritic cell homeostasis." Blood (2009) 113(15): 3418-3427.
Skokos, D., et al. "CD8- DCs induce IL-12-independent TH1 differentiation through Delta 4 Notch-like ligand in response to bacterial LPS." Journal of Experimental Medicine (2007) 204(7): 1525-1531.
Swee, L.K., et al. "Expansion of peripheral naturally occurring T regulatory cells by Fms-like tyrosine kinase 3 ligand treatment." Blood (2009) 113(25) 6277-6287.
"Progress in Autoimmune Disease Research," U.S. Department of Health and Human Services, National Institutes of Health, The Autoimmue Diseases Coordinating Committee, pp. 1-126, (2005). [No Author identified].
Chevalier et al., "The split personality of regulatory T cells in HIV infection," Blood, 121(1):29-37, (2013).
Fontana et al., "Narcolepsy: autoimmunity, effector T cell activation due to infection, or T cell independent, major histocompatibility complex class II induced neuronal loss?," Brain, 133:1300-1311, (2010).
Mukherjee al., "Regulation of T Cell Activation by Notch Ligand, DLL4, Promotes IL-17 Production and Rorc Activation," J. Immunol., 182:7381-7388, (2009).
Purow, "Notch Inhibition as a Promising New Approach to Cancer Therapy," Adv. Exp. Med. Biol., 727:305-319, (2012).
U.S. Appl. No. 13/015,637, Non-Final Office Action mailed Jul. 11, 2013.
U.S. Appl. No. 13/015,637, Requirement for Restriction/Election mailed Feb. 12, 2013.
WIPO Application No. PCT/US2011/022810, PCT International Preliminary Report on Patentability mailed Aug. 19, 2012.
WIPO Application No. PCT/US2011/022810, PCT International Search Report mailed May 26, 2011.
WIPO Application No. PCT/US2011/022810, PCT Written Opinion of the International Searching Authority mailed May 26, 2011.
WIPO Application No. PCT/US2011/022817, PCT International Preliminary Report on Patentability mailed Aug. 9, 2012.
WIPO Application No. PCT/US2011/022817, PCT International Search Report mailed Oct. 28, 2011.
WIPO Application No. PCT/US2011/022817, PCT Written Opinion of the International Searching Authority mailed Oct. 28, 2011.

* cited by examiner

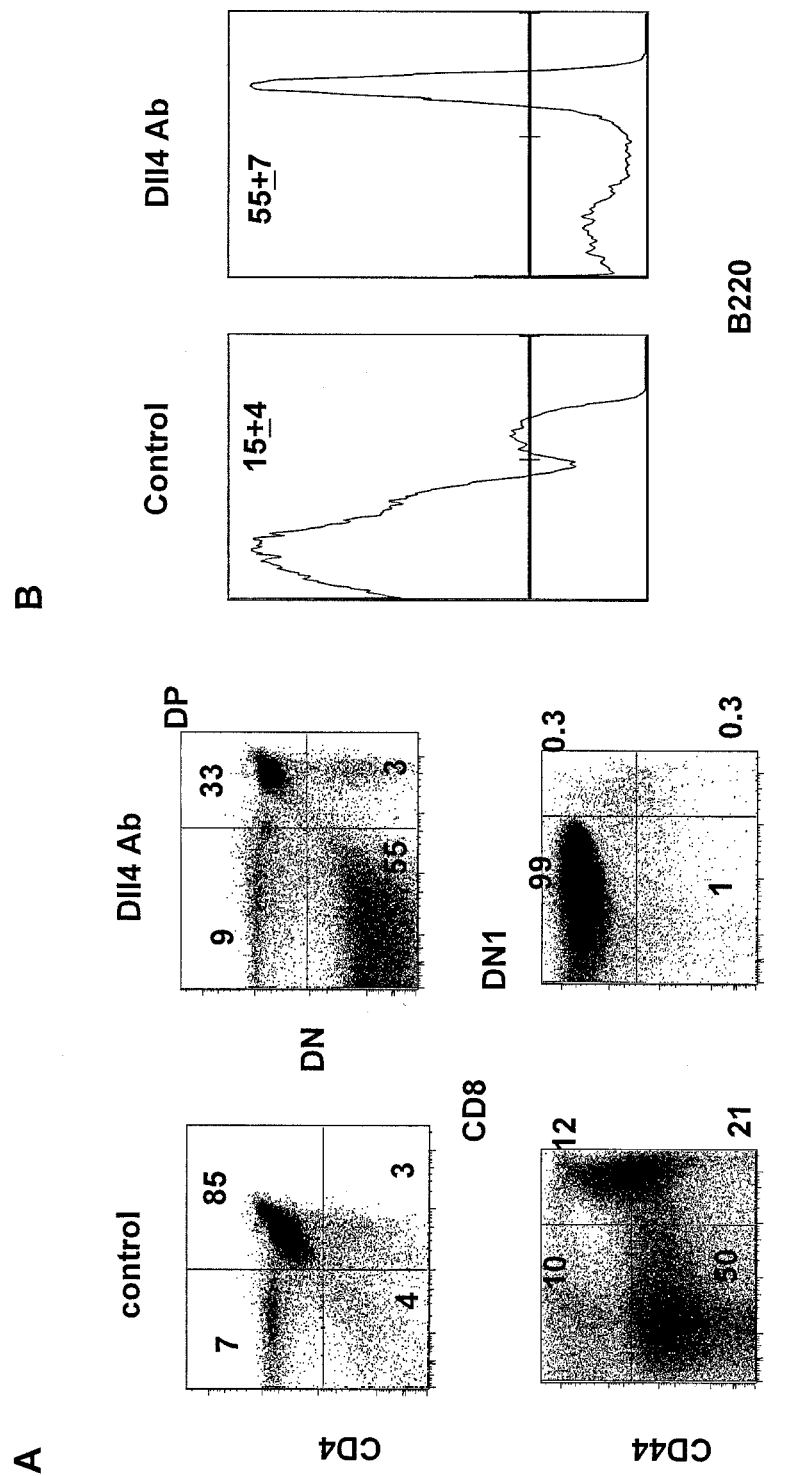
Fig. 1A-B

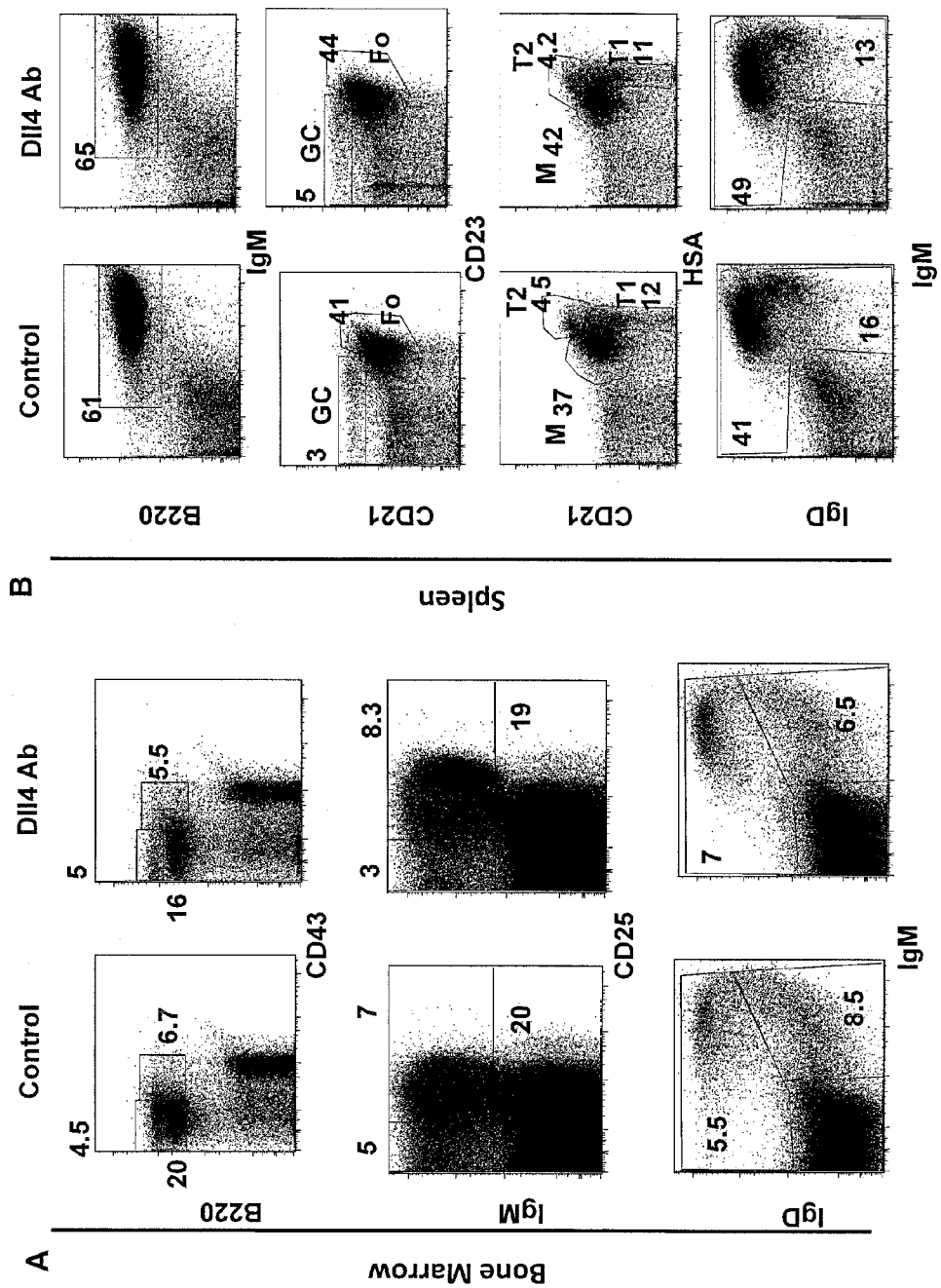
Fig. 2A-B

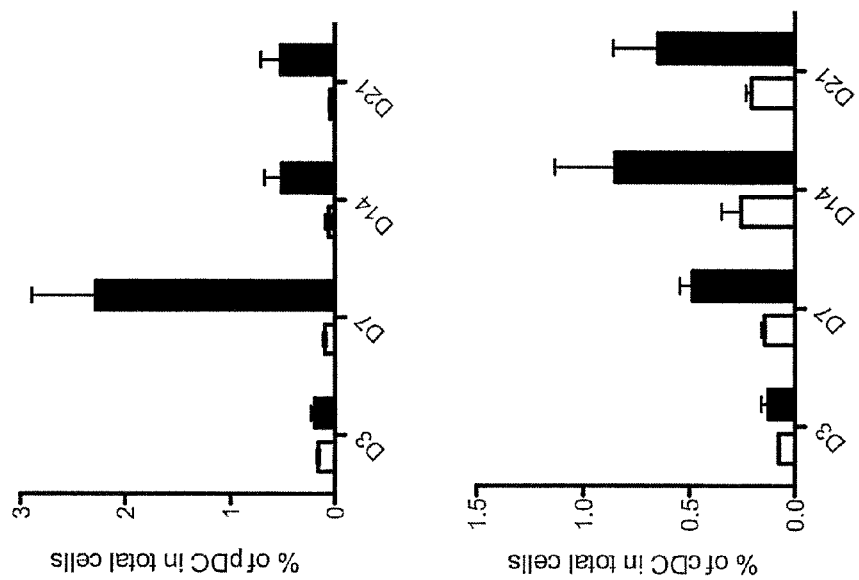

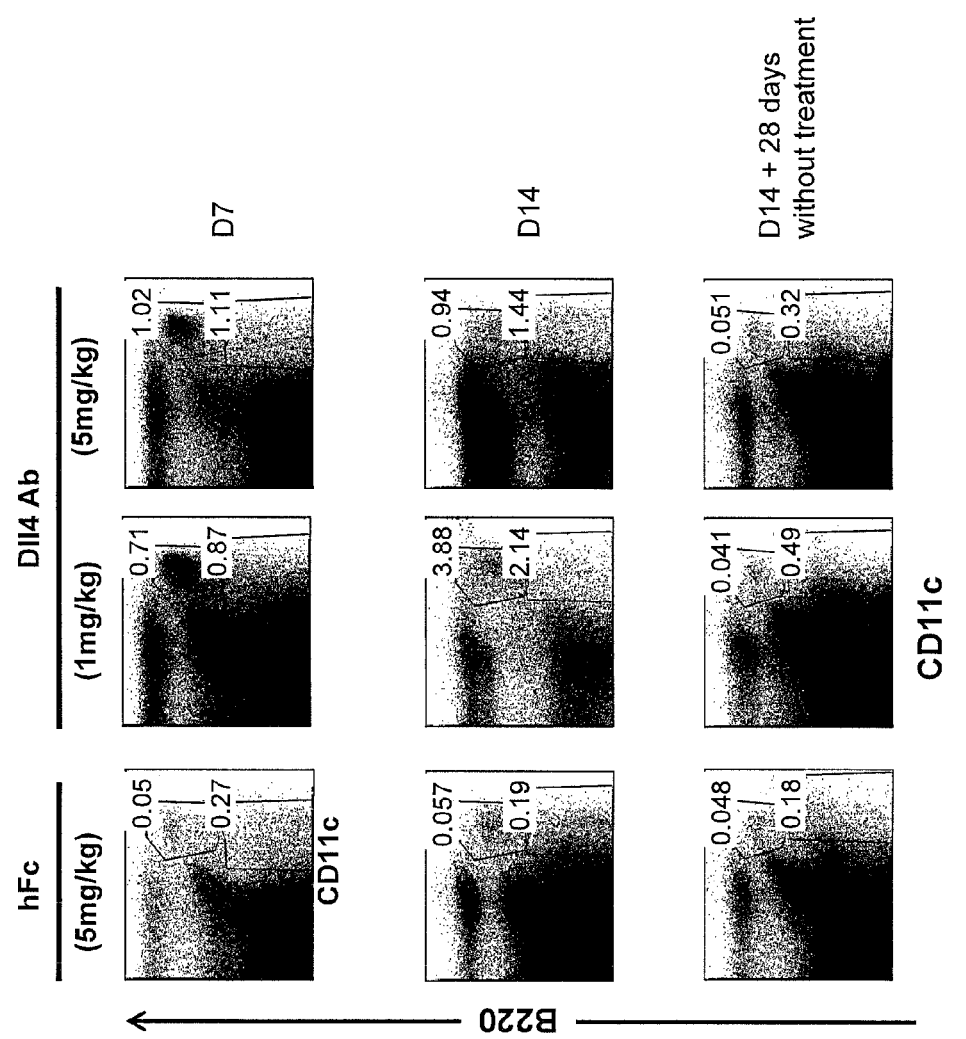

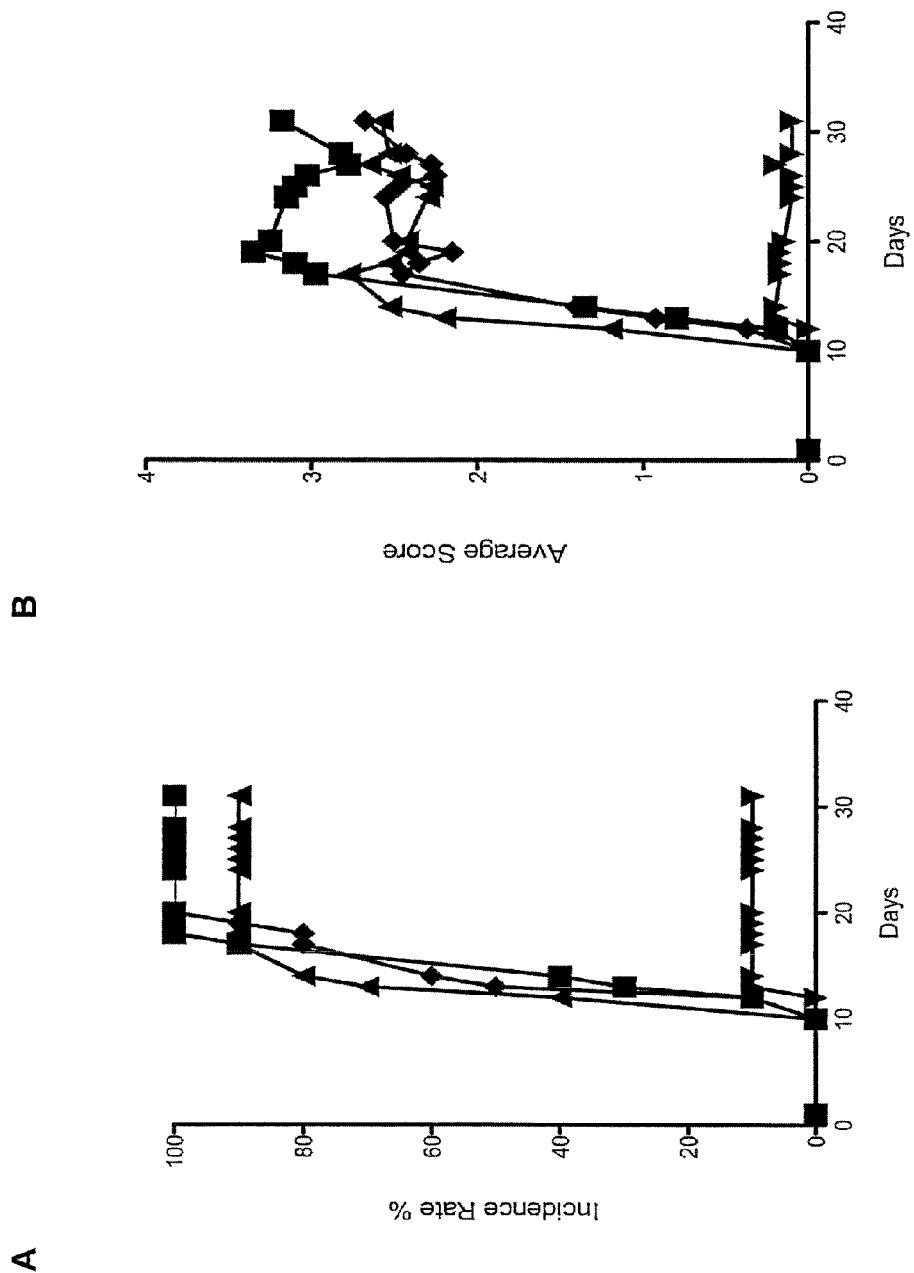
Fig. 9A-B

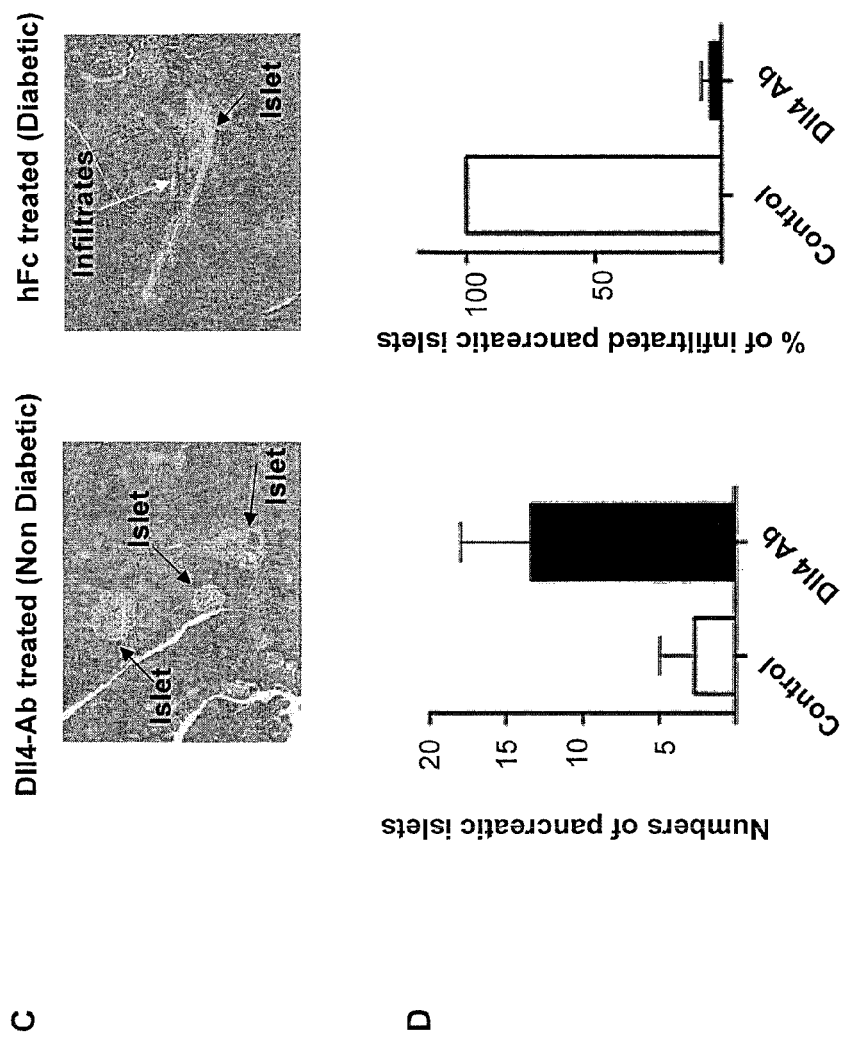
Fig. 11C-D

METHODS OF TREATING DIABETES WITH DLL4 ANTAGONISTS

CROSS-REFERENCE TO RELATED APPLICATIONS

This application claims the benefit under 35 U.S.C §119(e) of U.S. provisional application Nos. 61/299,801 filed Jan. 29, 2010; 61/361,687 filed Jul. 6, 2010; and 61/388,697 filed Oct. 1, 2010, all of which are herein specifically incorporated by reference in their entirety.

BACKGROUND OF THE INVENTION

1. Field of the Invention

This invention relates to methods of treating a disease, disorder, or condition, in which increasing the number of regulatory T cells (Treg cells or Tregs) is beneficial, using delta-like ligand 4 (Dll4) antagonists. More specifically, the methods of the invention can prevent, treat or ameliorate diabetes by blocking the binding of Dll4 to a Notch receptor with Dll4 antagonists, thereby increasing the number of Tregs. Furthermore, the invention relates to methods of lowering blood glucose levels, or reducing or blocking the production of auto-antibodies, including those against insulin and glutamic acid decarboxylase 65 (GAD65), respectively, with Dll4 antagonists.

2. Description of Related Art

Interactions between Notch receptors and their ligands represent an evolutionarily conserved pathway important not only for cell fate decisions but also in regulating lineage decisions in hematopoiesis and in the developing thymus (Artavanis-Tsakonas et al. 1999, *Science* 284:770-776; Skokos et al. 2007; *J Exp Med* 204:1525-1531; and Amsen et al. 2004, *Cell* 117:515-526). It has been recently shown that Dll4-Notch1 inhibition leads to a complete block in T cell development accompanied by ectopic appearance of B cells and an expansion of dendritic cells (DC) that can arise from Pro-T cell to DC fate conversion within the thymus (Hozumi et al. 2008, *J Exp Med* 205(11):2507-2513; Koch et al. 2008, *J Exp Med* 205(11):2515-2523; and Feyerabend et al. 2009, *Immunity* 30:1-13). Thus, there is accumulating evidence that Notch signaling is critical for the determination of cell fate decision from hematopoietic progenitor cells. Furthermore, a feedback control of regulatory T cell (Treg) homeostasis by DCs in vivo has been shown (Darrasse-Jéze et al. 2009, *J Exp Med* 206(9):1853-1862). However, the role of Notch signaling in controlling the origin and the development of DCs and consequently Treg homeostasis is still unknown. This is a question clinically important because identifying new methods of inducing Treg expansion could be used as a treatment for autoimmunity diseases and disorders.

The nucleic acid and amino acid sequences of human Dll4 (hDll4) are shown in SEQ ID NOS:1 and 2, respectively. Dll4 antagonists and their uses are disclosed in WO 2007/143689, WO 2007/070671, WO 2008/076379, WO 2008/042236, and WO/2008/019144.

BRIEF SUMMARY OF THE INVENTION

The present invention is based in part on the observation by the present inventor that an antibody, which specifically binds Dll4 and blocks Dll4 binding to Notch receptors, is able to fully prevent a progression of Experimental Autoimmune Encephalomyelitis (EAE) in mice, an animal model for human multiple sclerosis, while a control antibody does not prevent EAE. Furthermore, the present inventor has discovered that this effect of anti-Dll4 antibody is associated with the increased number of Treg cells. In addition, it has been further observed that an anti-Dll4 antibody prevents an increase in blood glucose level and preserves the number and morphology of pancreatic islets in NOD/ShiLtJ mice, an animal model for type 1 diabetes, and such effects are, at least in part, mediated by the expansion of Tregs.

Thus, in a first aspect, the invention features a method of increasing the number of Treg cells, comprising administering an effective amount of a Dll4 antagonist to a subject in need thereof, wherein the Dll4 antagonist blocks the interaction between Dll4 and a Notch receptor and the number of Treg cells is increased.

In a second aspect, the invention features a method of preventing, treating or ameliorating a disease, disorder, or condition in which increasing the number of Treg cells is beneficial, comprising administering a therapeutically effective amount of a Dll4 antagonist to a subject in need thereof. The disease or disorder treatable by the methods of the invention is any disease, disorder, or condition which is benefitted, i.e., improved, ameliorated, inhibited or prevented by removal, inhibition or reduction of Dll4 activity, thereby increasing the number of Treg cells in the treated subject. One of such diseases or disorders treatable by the method of the invention is diabetes, i.e., diabetes mellitus type 1 and type 2. Thus, in one embodiment, the invention provides a method of preventing, treating or ameliorating diabetes mellitus type 1 or type 2, comprising administering to a subject in need thereof a therapeutically effective amount of a Dll4 antagonist.

In a third aspect, the invention features a method of lowering blood glucose levels, comprising administering to a subject in need thereof a therapeutically effective amount of a Dll4 antagonist.

In a fourth aspect, the invention features a method of reducing or blocking the production of auto-antibodies, comprising administering to a subject in need thereof a therapeutically effective amount of a Dll4 antagonist. Auto-antibodies may include those against insulin, those against GAD65, and the like.

In one embodiment, the Dll4 antagonist to be used in any of the methods of the invention described above is a Dll4 antibody or fragment thereof ("anti-Dll4 Ab" or "Dll4 Ab") that specifically binds Dll4 with high affinity and blocks the binding of Dll4 to the Notch receptors and/or blocks the Dll4-Notch signal pathways. The antibody may be polyclonal, monoclonal (mAb), chimeric, humanized, or a wholly human antibody or fragment thereof. The antibody fragment may be a single chain antibody, an Fab, or an (Fab')$_2$.

In one embodiment, the Dll4 Ab or antigen-binding fragment thereof binds an epitope within the N-terminal domain (residues S27-R172), or the Delta/Serrate/Lag-2 (DSL) domain (residues V173-C217), or the N-terminal-DSL domain (residues S27-C217), of hDll4 (SEQ ID NO:2). In another embodiment, the Dll4 Ab or antigen-binding fragment thereof binds an epitope within one of the EGF domains, i.e., at about amino acid residues Q218-N251 (domain 1), E252-D282 (domain 2), D284-E322 (domain 3), E324-E360 (domain 4), 5362-E400 (domain 5), K402-E438 (domain 6), H440-E476 (domain 7), or 5480-E518 (domain 8), of hDll4 (SEQ ID NO:2). In some embodiments, the antibody or antibody fragment may bind a conformational epitope involving more than one of the epitopes enumerated above. The Dll4 Ab or fragment thereof to be used in the methods of the invention is capable of binding human Dll4 with high affinity and has an equilibrium dissociation constant ($K_D$) of about 1 nM or less, about 500 pM or less, about 300 pM or less, about 200 pM or less, about 100 pM or less, or about 50 pM or less, as measured by surface plasmon resonance.

In one embodiment, the Dll4 Ab or fragment thereof comprises a heavy chain variable region (HCVR) comprising three heavy chain complementarity determining regions, HCDR1, HCDR2 and HCDR3, having the amino acid sequences of SEQ ID NOS: 22, 24 and 26, respectively. In another embodiment, the antibody or fragment thereof comprises a light chain variable region (LDVR) comprising three light chain complementarity determining regions, LCDR1, LCDR2 and LCDR3, having the amino acid sequences of SEQ ID NOS:30, 32 and 34, respectively. In another embodiment, the Dll4 Ab or fragment thereof comprises the heavy and light chain CDR sequences comprising a CDR sequence combination of SEQ ID NOS:22, 24, 26, 30, 32 and 34. In yet another embodiment, the Dll4 Ab comprises a HCVR comprising the amino acid sequence of SEQ ID NO:20 or 116, or a LCVR comprising the amino acid sequence of SEQ ID NO:28 or 118. In yet another embodiment, the Dll4 Ab comprises a HCVR/LCVR combination of SEQ ID NO:20/28 (REGN281) or 116/118 (REGN421).

In certain embodiments, the Dll4 Ab comprises a heavy chain CDR1/CDR2/CDR3 combination and a light chain CDR1/CDR2/CDR3 combination selected from: SEQ ID NO:6/8/10 and SEQ ID NO:14/16/18, respectively; SEQ ID NO:38/40/42 and SEQ ID NO:46/48/50, respectively; SEQ ID NO:54/56/58 and SEQ ID NO:62/64/66, respectively; SEQ ID NO:70/72/74 and SEQ ID NO:78/80/82, respectively; SEQ ID NO:86/88/90 and SEQ ID NO:94/96/98, respectively; and SEQ ID NO:102/104/106 and SEQ ID NO:110/112/114, respectively. In another embodiment, the Dll4 Ab comprises a HCVR comprising the amino acid sequence of SEQ ID NO:4, 36, 52, 68, 84, or 100, or a LCVR comprising the amino acid sequence of SEQ ID NO:12, 44, 60, 76, 92, or 108. In yet another embodiment, the Dll4 Ab comprises a HCVR/LCVR combination selected from: SEQ ID NO:4/12 (REGN279); SEQ ID NO:36/44 (REGN290); SEQ ID NO:52/60 (REGN306); SEQ ID NO:68/76 (REGN309); SEQ ID NO:84/92 (REGN310); and SEQ ID NO:100/108 (REGN289).

The nucleotide sequences encoding the amino acid sequences of SEQ ID NOS:4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116 and 118, are shown as SEQ ID NOS:3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115 and 117, respectively.

In another embodiment, the Dll4 antagonist suitable in the methods of the invention is a fusion protein comprising at least one soluble Notch receptor or fragment thereof capable of binding Dll4, fused to a multimerizing component. In one embodiment, the soluble Notch receptor is human Notch1 or Notch4. In another embodiment, the Dll4 antagonist of the invention is a modified Dll4 protein that is capable of binding the Notch receptor(s) but such binding does not result in activation of the receptor(s). In certain embodiments, the Dll4 antagonist of the invention is a fusion protein comprising the extracellular domain of Dll4 or a fragment thereof fused to a multimerizing component, such as an immunoglobulin domain, for example, an Fc domain of a human IgG. In certain embodiments, the Dll4 antagonists include small molecules and other agents that can block Dll4-Notch interactions.

In a fifth aspect, the invention features any of the methods described above, wherein a Dll4 antagonist is coadministered concurrently or sequentially with at least one additional therapeutic agent, for example, a blood glucose lowering agent (e.g., insulin, insulin analogues, and the like), immunosuppressive agent or immunosuppressant, anti-inflammatory agent, analgesic agent, and the like, many of which may have overlapping therapeutic effects of one another. Suitable immunosuppressants to be used in combination with the Dll4 antagonist include, but are not limited to, glucocorticoids, cyclosporin, methotrexate, interferon β (IFN-β), tacrolimus, sirolimus, azathioprine, mercaptopurine, opioids, mycophenolate, TNF-binding proteins, such as infliximab, eternacept, adalimumab, and the like, cytotoxic antibiotics, such as dactinomycin, anthracyclines, mitomycin C, bleomycin, mithramycin, and the like, antibodies targeting immune cells, such as anti-CD20 antibodies, anti-CD3 antibodies, and the like. Suitable anti-inflammatory agents and/or analgesics for combination therapies with anti-Dll4 antagonists include, corticosteroids, non-steroidal anti-inflammatory drugs (NSAIDs), such as aspirin, ibuprofen, naproxen and the like, TNF-α antagonists, IL-1 antagonists, IL-6 antagonists, acetaminophen, morphinomimetics, and the like.

In a sixth aspect, the invention features a pharmaceutical composition comprising a Dll4 antagonist, at least one additional therapeutic agent, and a pharmaceutically acceptable carrier. In one embodiment, the Dll4 antagonist is a Dll4 Ab or fragment thereof that specifically binds to Dll4 with high affinity and neutralizes Dll4 activities, and at least one additional therapeutic agent is any of the glucose lowering agents, immunosuppressants, anti-inflammatory agents, analgesics, and the like, described above.

In a seventh aspect, the invention features a kit comprising a container comprising the pharmaceutical composition of the present invention, and a package insert with an instruction for use. In one embodiment, a kit may comprise a container comprising therein an antibody or fragment thereof that specifically binds hDll4, another container comprising therein at least one additional therapeutic agent described above.

Other objects and advantages will become apparent from a review of the ensuing detailed description.

BRIEF DESCRIPTION OF THE FIGURES

FIG. 1A-1B show the effects of Dll4 blockade on the development of T cells and B cells. Mice were injected with anti-Dll4 antibody (REGN577) or control human Fc fragment (hFc). Fourteen days later, thymi were harvested and T-cell and B-cell subsets were evaluated by flow cytometry. FIG. 1A: Dot plots show the number of CD4$^-$CD8$^-$ (double negative thymic precursors or "DN"), CD4$^+$CD8$^+$ (double positive thymic precursors or "DP"), CD4$^+$ or CD8+ (single positive thymic precursors or "SP"), and DN/CD44$^+$CD25$^-$ (thymic precursors at the DN1 stage) T cells. The numbers in the dot plots represent percentages (mean±SEM) of T cell subpopulations among the total thymic cells. FIG. 1B: Histograms show the percentage (mean±SD) of B cells (B220$^+$) among DN1 cells (i.e., gated on CD4$^-$CD8$^-$CD44$^+$CD25$^-$).

FIG. 2A-2B show the effects of Dll4 blockade on B cell developmental stages in the bone marrow (FIG. 2A) and on B cell homeostasis in the spleen (FIG. 2B). The numbers in the dot plots represent percentages (mean±SEM) of B cell subsets among the total cells in bone marrow or in spleen. GC: Germinal center B cells; T1 and T2: B cell subsets; M: Marginal B cells; and Fo: Follicular B cells.

FIG. 3A-3D show the effects of Dll4 blockade on dendritic cell (DC) development. FIG. 3A: Dot plots show the expansion of conventional DCs ("cDCs"; B220$^-$CD11C$^+$) and plasmacytoid DCs ("pDCs"; PDCA1$^+$B220$^+$CD11C$^+$) in the thymus upon anti-Dll4 Ab treatment. Numbers in dot plots represent average percentages (mean±SEM) of DCs among total cells at day 14. FIG. 3B: The bar graphs show the kinetics of cDC and pDC expansion in the thymus of Dll4 Ab-treated mice (■) and hFc-control treated mice (□). FIG. 3C: Dot plots show the effects of Dll4 Ab on pre-DCs (MHCII$^{lo}$CD11c$^{int}$CD135$^+$Sirp-α$^{int}$) and late pre-DCs (MHCII$^{lo}$CD11c$^{int}$) in the thymus. Numbers in dot plots represent average percentages (mean±SEM) of pre-DCs among total cells at day 14. FIG. 3D: Dot plots show the presence of MHCII$^{lo}$CD11c$^{int}$ DCs in the DN1 (CD4$^-$CD8$^-$CD44$^+$CD25$^-$) pro-T cell population in the thymus of mice treated with Dll4 Ab, but not in the thymus of mice treated with hFc control Ab. Numbers in dot plots represent average number (mean±SEM) of MHCII$^{lo}$CD11c$^{int}$ DCs among DN1 pro-T cell population at day 3.

FIG. 7A: Dot plots show an expansion of Tregs within the thymus of mice treated with Dll4-Ab for two weeks, compared to mice treated with hFc control Ab. Numbers in dot plots represent average percentages (mean±SEM) of Tregs among CD3$^+$CD4$^+$ T cells in the thymus. FIG. 7B: Bar graphs show the kinetics of Treg development in thymus (upper panel) and spleen (lower panel), respectively, of the mice treated with Dll4 Ab (■) and hFc control Ab (□). FIG. 7C: Dot plots show an expansion of Tregs within the thymus of DLL4COIN mice treated with tamoxifen (TAM), compared to control DLL4COIN treated with corn oil control. Numbers in dot plots represent average percentages (mean±SEM) of Tregs among CD3$^+$CD4$^+$ T cells in the thymus.

FIG. 8A-8B show the effects of Dll4 blockade on DC (FIG. 8A) and Treg homeostasis (FIG. 8B) in the thymus of mice expressing human Dll4 (hDll4) observed at days 7 and 14 after Dll4-Ab (REGN421) treatment (1 mg/kg or 5 mg/kg) or hFc treatment (5 mg/kg), twice per week for 2 weeks and at day 28 after the cessation of treatment. Numbers in dot plots represent average percentages (mean±SEM) of pDCs and cDCs (FIG. 8A) or Tregs (FIG. 8B) among total cells in the thymus.

FIG. 9A-9B show the effects of Dll4 blockade in Experimental Autoimmune Encephalomyelitis (EAE) mouse model. FIG. 9A: The graph shows EAE disease incidence rates (%) per treatment group. FIG. 9B: The graph shows the development of EAE based on average disease scores. Treatment was with anti-Dll4 Ab (REGN577) pre-induction (▼); isotype control Ab pre-induction (♦); REGN577 post-induction (▲); or anti-VLA-4 Ab (PS/2) pre-induction (■).

FIG. 11A-11E show the effects of Dll4 Ab in a NOD mouse diabetic model. FIG. 11A shows the % diabetes incidence (two consecutive readings of blood glucose level higher than 250 mg/dL) among the mice that received either hFC control Ab (●) or anti-Dll4 Ab (REGN577) (■) at 9 weeks of age. The % diabetes incidence of five mice that had been treated with the Dll4 Ab and subsequently injected with PC61 Ab at 20 weeks is also shown (♦). PC61 Ab is an anti-CD25 antibody and depletes Treg cells. FIG. 11B shows the measurement by ELISA of anti-insulin autoantibody (□) and anti-glutamic acid decarboxylase 65 (GAD65) autoantibody (■) productions in NOD mice treated with Dll4 Ab or hFc control, compared to untreated wild type (WT) mice. FIG. 11C shows pancreatic sections stained with Hematoxylin and Eosin (H&E) of NOD mice treated with Dll4 Ab (left panel) or hFc control (right panel). Black arrows indicate individual pancreatic islets and white arrow indicates infiltrating cells within the islet (right panel). FIG. 11D shows the number of pancreatic islets (left panel) or % of infiltrated pancreatic islets (right panel) in the pancreas of hFc control-treated (□) or Dll4 Ab-treated (■) mice. FIG. 11E shows the changes in blood glucose level in mice treated, at the onset of the disease, with Dll4 Ab (●) or hFc control (□), over 42 days after the treatment.

DETAILED DESCRIPTION

Figure 3A:
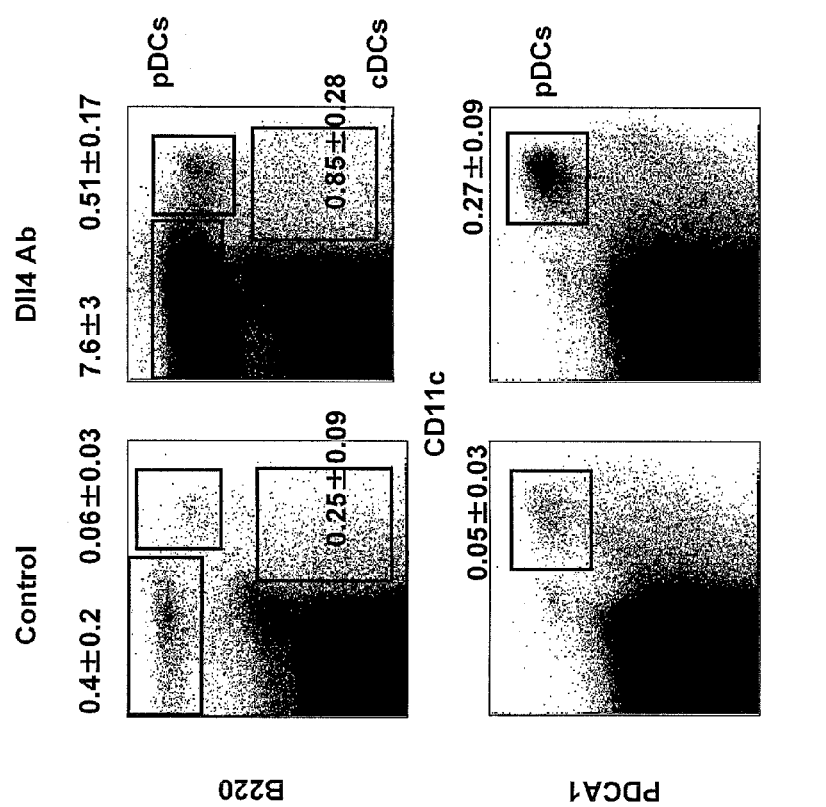

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

DEFINITIONS

The term "Dll4 antagonists", as used herein, include antibodies to Dll4 and fragments thereof capable of blocking the binding of Dll4 to a Notch receptor (such as Notch1 and Notch4) and/or blocking Dll4-Notch signal pathways (see, for example, WO 2008/076379), fusion proteins comprising the extracellular domain of Dll4 fused to a multimerizing component, or fragments thereof (see for example, US patent publication nos. 2006/0134121 and 2008/0107648), peptides and peptibodies (see, for example, U.S. Pat. No. 7,138,370), and the like, which block the interaction between Dll4 and a Notch receptor. Thus, in certain embodiments, the term also encompasses antagonists, such as small molecules, antibodies or antigen-binding fragments thereof, and the like, that specifically bind Notch receptors (e.g., anti-Notch1 antibodies, anti-Notch4 antibodies, etc.) and block Dll4-Notch signal pathways.

The term "antibody", as used herein, is intended to refer to immunoglobulin molecules comprised of four polypeptide chains, two heavy (H) chains and two light (L) chains interconnected by disulfide bonds. Each heavy chain is comprised of a heavy chain variable region (abbreviated herein as HCVR or $V_H$) and a heavy chain constant region ($C_H$). The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4.

Methods and techniques for identifying CDRs within HCVR and LCVR amino acid sequences are known in the art and can be applied to identify CDRs within the specified HCVR and/or LCVR amino acid sequences disclosed herein. Conventions that can be used to identify the boundaries of CDRs include the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273: 927-948 (1997); and Martin et al., *Proc. Natl. Acad. Sci. USA* 86:9268-9272 (1989). Public databases are also available for identifying CDR sequences within an antibody Substitution of one or more CDR residues or omission of one or more CDRs is also possible. Antibodies have been described in the scientific literature in which one or two CDRs can be dispensed with for binding. Padlan et al. (1995 FASEB J. 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al. 2002 J Mol Biol 320:415-428).

CDR residues not contacting antigen can be identified based on previous studies (for example, residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "antibody" also encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al. (2002) JBC 277:26733). In other applications, removal of N-glycosylation site may reduce undesirable immune reactions against the therapeutic antibodies, or increase affinities of the antibodies. In yet other applications, modification of galactosylation can be made in order to modify complement dependent cytotoxicity (CDC).

The term "antigen-binding fragment" of an antibody (or simply "antibody fragment"), as used herein, refers to one or more fragments of an antibody that retain the ability to specifically bind to hDll4, or any other intended target proteins. An antibody fragment may include a Fab fragment, a F(ab')$_2$ fragment, a Fd fragment, a Fv fragment, a single-chain Fv (scFv) molecule, a dAb fragment, minimal recognition units consisting of the amino acid residues that mimic the hypervariable region of an antibody (e.g., a fragment containing a CDR, or an isolated CDR). Other engineered molecules, such as diabodies, triabodies, tetrabodies and minibodies, are also encompassed within the expression "antigen-binding fragment", as used herein. In certain embodiments, antibody or antibody fragments of the invention may be conjugated to a therapeutic moiety ("immunoconjugate"), such as a cytotoxin, a chemotherapeutic drug, an immunosuppressant or a radioisotope.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format may be adapted for use in the context of an antigen-binding fragment of an antibody of the present invention using routine techniques available in the art.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-Dll4 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residues(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline back-mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residues of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Dll4 antibodies comprising variants of any of the HCVR, LCVR, and/or CDR amino acid sequences disclosed herein having one or more conservative substitutions. For example, the present invention includes anti-Dll4 antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein. In one embodiment, a HCVR comprises the amino acid sequence of SEQ ID NO:116 with 10 or fewer conservative amino acid substitutions therein. In another embodiment, a HCVR comprises the amino acid sequence of SEQ ID NO:116 with 8 or fewer conservative amino acid substitutions therein. In another embodiment, a HCVR comprises the amino acid sequence of SEQ ID NO:116 with 6 or fewer conservative amino acid substitutions therein. In another embodiment, a HCVR comprises the amino acid sequence of SEQ ID NO:116 with 4 or fewer conservative amino acid substitutions therein. In yet another embodiment, a HCVR comprises the amino acid sequence of SEQ ID NO:116 with 2 or 1 conservative amino acid substitution(s) therein. In one embodiment, a LCVR comprises the amino acid sequence of SEQ ID NO:118 with 10 or fewer conservative amino acid substitutions therein. In another embodiment, a LCVR comprises the amino acid sequence of SEQ ID NO:118 with 8 or fewer conservative amino acid substitutions therein. In another embodiment, a LCVR comprises the amino acid sequence of SEQ ID NO:118 with 6 or fewer conservative amino acid substitutions therein. In another embodiment, a LCVR comprises the amino acid sequence of SEQ ID NO:118 with 4 or fewer conservative amino acid substitutions therein. In yet another embodiment, a LCVR comprises the amino acid sequence of SEQ ID NO:118 with 2 or 1 conservative amino acid substitution(s) therein.

A "neutralizing" or "blocking" antibody, is intended to refer to an antibody whose binding to Dll4 results in inhibition of the biological activity of Dll4. This inhibition of the biological activity of Dll4 can be assessed by measuring one or more indicators of Dll4 biological activity. These indicators of Dll4 biological activity can be assessed by one or more of several standard in vitro or in vivo assays known in the art. For instance, the ability of an antibody to neutralize Dll4 activity is assessed by inhibition of Dll4 binding to a Notch receptor. Likewise, the term is also applicable to antibodies against other targets, such as Notch1 and Notch4; such antibodies inhibit the biological activities of the targets, thereby inhibiting Dll4-Notch interactions or signal pathways.

The term "specifically binds," or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. An isolated antibody that specifically binds hDll4 may, however, exhibit cross-reactivity to other antigens such as Dll4 molecules from other species. Moreover, multi-specific antibodies (e.g., bispecifics) that bind to hDll4 and one or more additional antigens are nonetheless considered antibodies that "specifically bind" hDll4, as used herein.

The term "$K_D$", as used herein, is intended to refer to the equilibrium dissociation constant of a particular antibody-antigen interaction.

The term "high affinity" antibody refers to those antibodies that bind Dll4 with a $K_D$ of about 1 nM or less, about 500 pM or less, about 400 pM or less, about 300 pM or less, about 200 pM or less, or about 100 pM or less, or about 50 pM or less, as measured by surface plasmon resonance, e.g., BIA-CORE™ or solution-affinity ELISA.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. An epitope typically includes at least 3, and more usually, at least 5 or 8-10 amino acids in a unique spatial conformation.

The term "treatment" or "treat", as used herein, is intended to mean both prophylactic (or preventative) and therapeutic procedures, unless otherwise indicated. Subjects in need of treatment include not only those who have developed a particular condition, disorder or disease, but also those who are predisposed or susceptible to developing such a condition, disorder or disease and are benefited by prophylactic procedures so that the occurrences or recurrences, or the progression, if it occurs, of such a condition, disorder or disease are reduced, compared with those in the absence of the treatment.

By the phrase "therapeutically effective amount", "prophylactically effective amount", or "effective amount" is meant an amount that produces the desired effect for which it is administered. The exact amount will depend on the purpose of the treatment, the age and the size of a subject treated, the route of administration, and the like, and will be ascertainable by one skilled in the art using known techniques (see, for example, Lloyd (1999) The Art, Science and Technology of Pharmaceutical Compounding).

GENERAL DESCRIPTION

The present invention is based in part on the findings that the blockade of Dll4 by a Dll4-specific antibody results in the increased number of Treg cells, which, in turn, prevents, reduces, or delays a progression of EAE or diabetes in mice. For a description of fully human Dll4 Ab, including recombinant human Dll4 Ab, see International Patent Publication No. WO 2008/076379.

Therapeutic Administration and Formulations

The present invention provides methods of preventing, treating or ameliorating a disease or disorder in which increasing the number of Treg cells is beneficial, comprising administering a therapeutically effective amount of a pharmaceutical composition comprising a Dll4 antagonist, such as a Dll4 Ab. The pharmaceutical composition comprising a Dll4 antagonist can further comprise one or more additional therapeutic agents, such as immunosuppressive agents, anti-inflammatory agents, analgesic agents, blood glucose lowering agents, and the like (see the following section). The therapeutic compositions in accordance with the invention can be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

The dose may vary depending upon the age and the size (e.g., body weight or body surface area) of a subject to be administered, target disease, conditions, route of administration, and the like. For systemic administration of Dll4 antagonists, in particular, for Dll4 antibodies, typical dosage ranges for intravenous administration are at a daily dose of about 0.01 to about 100 mg/kg of body weight, about 0.1 to about 50 mg/kg, or about 0.2 to about 10 mg/kg. For subcutaneous administration, the antibodies can be administered at about 1 mg to about 800 mg, about 10 mg to about 500 mg, about 20 mg to about 400 mg, about 30 mg to about 300 mg, or about 50 mg to about 200 mg, at the antibody concentration of, at least, about 25 mg/ml, about 50 mg/ml, about 75 mg/ml, about 100 mg/ml, about 125 mg/ml, about 150 mg/ml, about 175 mg/ml, about 200 mg/ml, or about 250 mg/ml, at least, 1 to 5 times per day, 1 to 5 times per week, or 1 to 5 times per month. Alternatively, the antibodies can be initially administered via intravenous injection, followed by sequential subcutaneous administration.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al. (1987) J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the Dll4 antagonist, such as a Dll4 antibody, contained is generally about 0.1 to about 800 mg per dosage form in a unit dose; especially in the form of injection, it is preferred that the antibody is contained in about 5 to about 100 mg and in about 10 to about 250 mg for the other dosage forms.

In a certain embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

Combination Therapies

In the therapeutic methods of the invention, a Dll4 antagonist may be provided alone or in combination with one or more additional therapeutic agents, such as immunosuppressive agents or immunosuppressants, anti-inflammatory agents, analgesic agents, direct or indirect blood glucose lowering agents, and the like. Suitable immunosuppressants include, but are not limited to, glucocorticoids, cyclosporin, methotrexate, interferon $\beta$ (IFN-$\beta$), tacrolimus, sirolimus, azathioprine, mercaptopurine, opioids, mycophenolate, TNF-binding proteins, such as infliximab, eternacept, adalimumab, and the like, cytotoxic antibiotics, such as dactinomycin, anthracyclines, mitomycin C, bleomycin, mithramycin, and the like, antibodies targeting immune cells, such as anti-CD20 antibodies, anti-CD3 antibodies, and the like. Suitable anti-inflammatory agents and/or analgesics for combination therapies with anti-Dll4 antagonists include, corticosteroids, non-steroidal anti-inflammatory drugs (NSAIDs), such as aspirin, ibuprofen, naproxen and the like, TNF-$\alpha$ antagonists (e.g., Infliximab or REMICADE® by Centocor Inc.; golimumab by Centocor Inc.; etanercept or ENBREL® by Amgen/Wyeth; adalimumab or HUMIRA® by Abbott Laboratories, and the like), IL-1 antagonists (e.g., IL-1-binding fusion proteins, for example, ARCALYST® by Regeneron Pharmaceuticals, Inc., see U.S. Pat. No. 6,927,044; KINERET® by Amgen, and the like), IL-6 antagonists (e.g., anti-IL-6 receptor antibodies as disclosed in U.S. Pat. No. 7,582,298, and ACTEMRA® by Roche), acetaminophen, morphinomimetics, and the like. Suitable glucose lowering agents include, but are not limited to, insulin and analogs thereof, biguanides, sulfonamides and urea derivatives thereof, alpha-glucosidase inhibitors, thiazolidinedione and derivatives thereof, dipeptidyl peptidase-4 inhibitors, guar gum, repaglinide, nateglinide, exenatide, pramlintide, benfluorex, liraglutide, mitiglinide, aldose reductase inhibitors, and the like.

The Dll4 antagonist, such as hDll4 Ab or fragment thereof, and the additional therapeutic agent(s) described above can be co-administered together or separately. Where separate dosage formulations are used, the antibody or fragment thereof of the invention and the additional agents can be administered concurrently, or separately at staggered times, i.e., sequentially, in appropriate orders.

Kits

The invention further provides an article of manufacturing or kit, comprising a packaging material, container and a pharmaceutical agent contained within the container, wherein the pharmaceutical agent comprises at least one Dll4 antagonist, such as Dll4 antibody, and at least one additional therapeutic agent, and wherein the packaging material comprises a label or package insert showing indications and directions for use.

In one embodiment, the Dll4 antagonist and the additional therapeutic agent may be contained in separate containers.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by weight, temperature is in degrees Centigrade, pressure is at or near atmospheric, and figure error bars=mean±SEM.

In the examples below, the following antibodies in Dulbecco's PBS (GIBCO® INVITROGEN™) 1× supplemented with 3% FCS, were used to stain cells for flow cytometry purpose: For DCs, antibodies against signal-regulatory protein α (Sirp-α; cat #P84; BD Biosciences), B220 (cat #RA3-6B2), PDCA-1 (cat #eBio927), CD8 (cat #53-6.7), CD11b (cat# M1/70), MHCII (cat #M5/114.15.2), CD11c (cat #N418), and CD135 (cat #A2F10), respectively; for T, B and NK cells, antibodies against CD4 (cat #GK1.5 or L3T4), CD3 (cat #145-2C11), CD25 (cat# PC61 or 7D4), CD44 (cat #IM7), FoxP3 (cat #FJK16s); and F4/80 (cat #BM8), NK1.1 (cat #PK136), IgM (catNo. II/41), IgD (cat #26-11c), CD43 (cat #S7), CD21 (cat #eBio4E3), HSA (cat #M1/69), and CD23 (cat #B3B4), respectively, (all from eBioscience).

Example 1

Effect of Dll4 Blockade on Development of B cells, Dendritic Cells and T Cells

It has been shown that Dll4-Notch1 inhibition leads to a complete block in T cell development accompanied by ectopic appearance of B cells and an expansion of dendritic cells (DC) that can arise from Pro-T cell to DC fate conversion within the thymus (Hozumi et al. 2008, *J Exp Med* 205(11):2507-2513; Koch et al., 2008, *J Exp Med* 205(11): 2515-2523; and Feyerabend et al. 2009, *Immunity* 30:1-13). It is, however, still unknown as to which specific stage of DC development is directly affected by the Dll4 blockade.

To answer this question, 6 week-old C57B1/6 mice (Jackson Labs) were injected subcutaneously with 5 or 25 mg/kg of anti-Dll4 Ab (REGN577) (n=5) or human Fc fragment (control) (n=5), twice a week for two weeks. REGN577 was prepared in-house based on the published sequence (WO 2007/143689). REGN 577 binds to human and mouse Dll4, but does not detectably binds human Dll1 and JAG1. Fourteen (14) days after the injection, thymi and spleens were harvested and digested at 37° C. for 30 min in complete RPMI 1640 medium (Invitrogen) supplemented with 10% fetal calf serum (FCS) and containing Collagenase D (Sigma Aldrich). To stop the reaction, 2 mM EDTA was added and the organ suspension was passed through a 70-mm cell strainer. Bone marrow (BM) was collected from each mouse by flushing femurs and tibias in complete RPMI 1640 medium supplemented with 10% FCS and cells were resuspended in RPMI medium. T cell, B cell and DC subsets were evaluated by flow cytometry after the cells were stained with the antibodies against specific markers described above. The stained cells were run on a BD™ LSR II Flow Cytometer (BD Biosciences) and the data were analyzed using FlowJo software (version 8.8.6; Tree Star Inc.).

FIGS. 1A and 1B show the T and B cell populations in the thymus. As shown in FIG. 1A, Dll4 blockade induced a significant increase in the number of double negative ("DN"; CD4$^-$CD8$^-$) T cells and a decrease in the number of double positive ("DP"; CD4$^+$CD8$^+$) T cells within the thymus. In addition, the same treatment induced an ectopic appearance of B cells within the thymus, which arose from Pro-T cells (i.e., CD44$^+$CD25$^-$CD4$^-$CD8$^-$ cells at DN1 stage) (see FIG. 1B). In contrast, Dll4 blockade had no effect on B cell development in the bone marrow (FIG. 2A) or in the peripheral splenic B cell subpopulations (FIG. 2B). Furthermore, Dll4 blockade induced expansion of conventional DCs ("cDCs"; B220$^-$CD11c$^+$) and plasmacytoid DCs ("pDCs"; PDCA1$^+$ B220$^+$CD11C$^+$) in the thymus (FIG. 3A), with significant expansion starting at day 7 (p<0.001) through day 14 (p<0.001) and continued through day 21 (p<0.01) (FIG. 3B) after the initial injection of Dll4 Ab. Numbers in dot plots of FIG. 3A represent average percentages of DCs among total cells at day 14. Further, DCs were expanded in the periphery of mice treated with Dll4 Ab (REGN577). Fold increases in percentage and absolute number of DCs in spleen upon treatment with Dll4 Ab, compared to the control mice (hFc-treated), are shown in Table 1.

TABLE 1

| Days after initial injection | Fold-increase in percentage | Fold-increase in absolute number |
| --- | --- | --- |
| 3 | 1.0 | 1.0 |
| 7 | 1.1 | 1.1 |
| 14 | 1.6 | 2.0 |
| 21 | 1.3 | 1.7 |

It is known that lymphoid tissue cDCs, pDCs and monocytes share a common progenitor called "macrophage and DC precursor" or "MDP", which can be identified by its surface phenotype "Lin$^-$cKit$^{hi}$CD115$^+$FLT3$^+$", while a distinct progenitor called "common DC precursor" or "CDP" with "Lin$^-$cKit$^{lo}$CD115$^+$FLT3$^+$" is restricted to producing cDCs and pDCs. Although monocytes can develop many of the phenotypic features of DCs under inflammatory conditions, the cDC, pDC and monocytes lineages separate by the time they reach tissues, and neither monocytes nor pDCs develop into cDCs under steady state conditions. Unlike monocytes and pDCs, cDCs in lymphoid tissue are thought to emerge from the bone marrow as immature cells that must further differentiate and divide in lymphoid organs. Pre-DCs (MHCII$^{lo}$CD11c$^{int}$CD135$^±$Sirp-α$^{int}$) and late pre-DCs (MHCII$^{lo}$CD11c$^{int}$, are precursors primarily to cDCs that arise in bone marrow (Liu et al., 2009, *Science* 324:392-397).

To identify any effect of Dll4 Ab on DC progenitor homeostasis, the levels of MDP and CDP in the thymus, the bone marrow and the spleen were evaluated by flow cytometry. MDP and CDP were only detected in the bone marrow, but neither in the thymus nor in the spleen (data not shown). Furthermore, Dll4 blockade did not induce expansion of early progenitors in bone marrow compared to the control-treated mice. Thus, the result suggested that the Dll4 Ab could act at a later stage, i.e., pre-DC stage, of DC development than MDP and CDP.

Figure 3C:
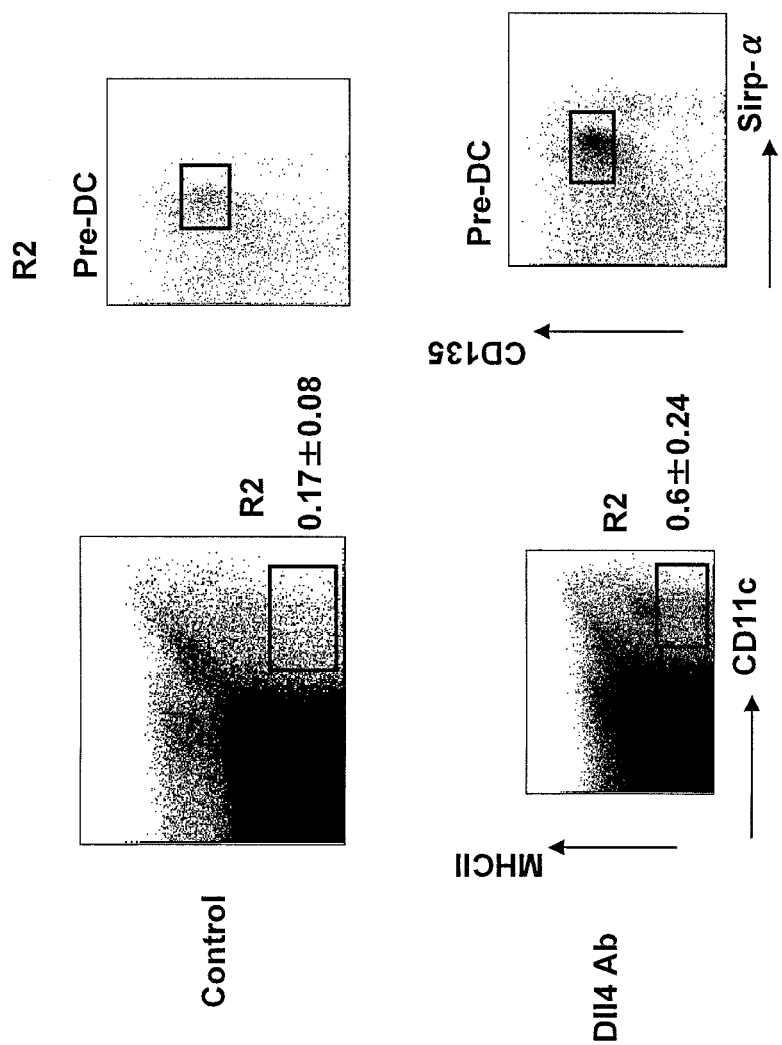
Figure 3D:
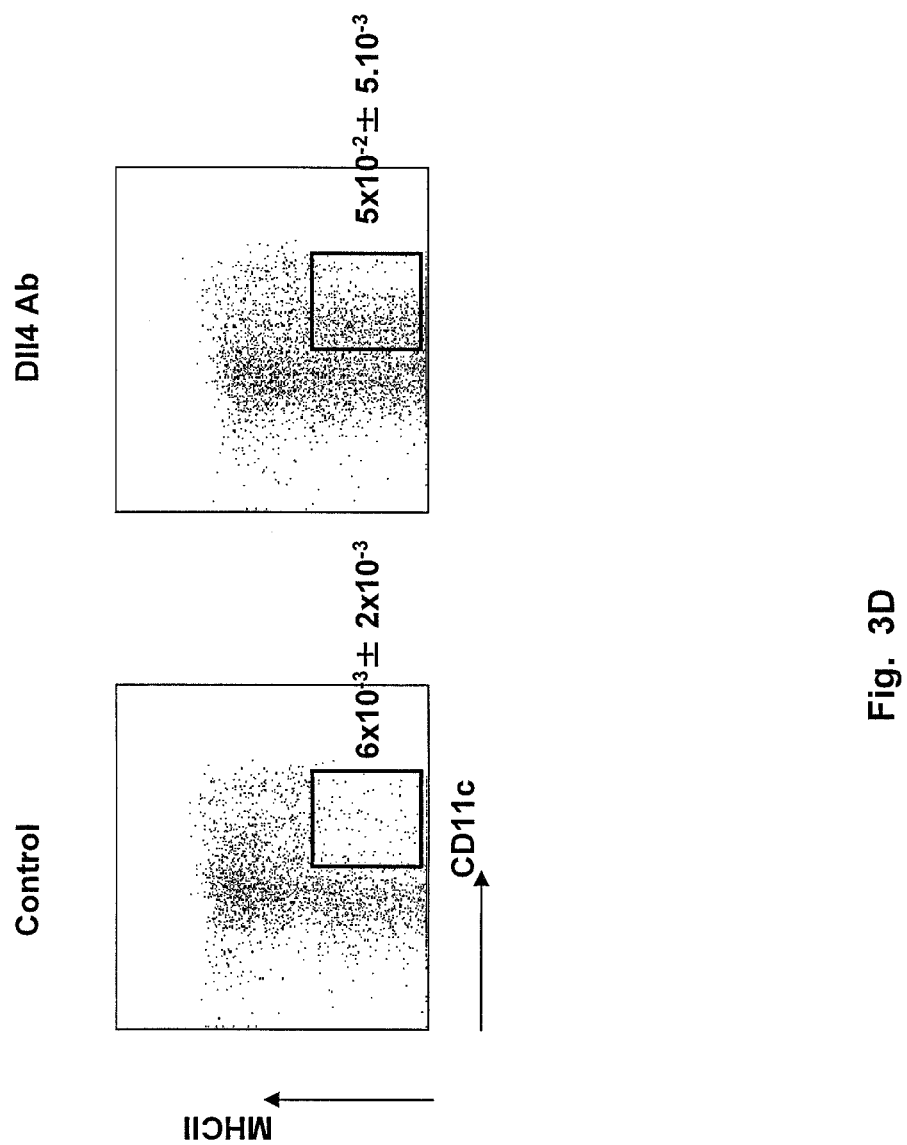

Accordingly, pre-DCs and late pre-DCs in the thymus and the bone marrow were searched for using the flow cytometry. As shown in FIG. 3C, MHCII$^{lo}$CD11c$^{int}$ DCs, which are normally present in the bone marrow, were only expanded in the thymus 14 days after the Dll4 Ab treatment (p<0.001), while no expansion of MHCII$^{lo}$CD11c$^{int}$ DCs was detected in the BM of the same mice (data not shown). Thus, the DC expansion originated from the pre-DC stage was restricted to thymus. To evaluate the origin of MHCII$^{lo}$CD11c$^{int}$ DCs in the thymus, flow cytometry was conducted to identify MHCII$^{lo}$CD11c$^{int}$ DCs in the DN1 (CD4$^-$CD8$^-$CD44$^+$CD25$^-$) pro-T cell population. As shown in FIG. 3D, MHCII$^{lo}$CD11c$^{int}$ DCs were detected within the DN1 pro-T cell population upon Dll4 blockade at day 3. No MHCII$^{lo}$CD11c$^{int}$ DCs were detected in the absence of Dll4 Ab treatment as well as within DN2, DN3 and DN4 T cell populations upon Dll4 Ab treatment (data not shown). No change in peripheral DC homeostasis was observed upon Dll4 Ab treatment (data not shown). Thus, Dll4 blockade induced a significant expansion of MHCII$^{lo}$CD11c$^{int}$ DCs within DN1 pro-T cell population in the thymus at day 3 ($p<0.01$) (FIG. 3D) with a peak of expansion at day 14 ($p<0.001$) (data not shown). Meanwhile, mature DC subsets expanded at day 7 ($p<0.001$) through day 21 ($p<0.01$) in the thymus, as discussed above (see FIG. 3B).

Figure 4:
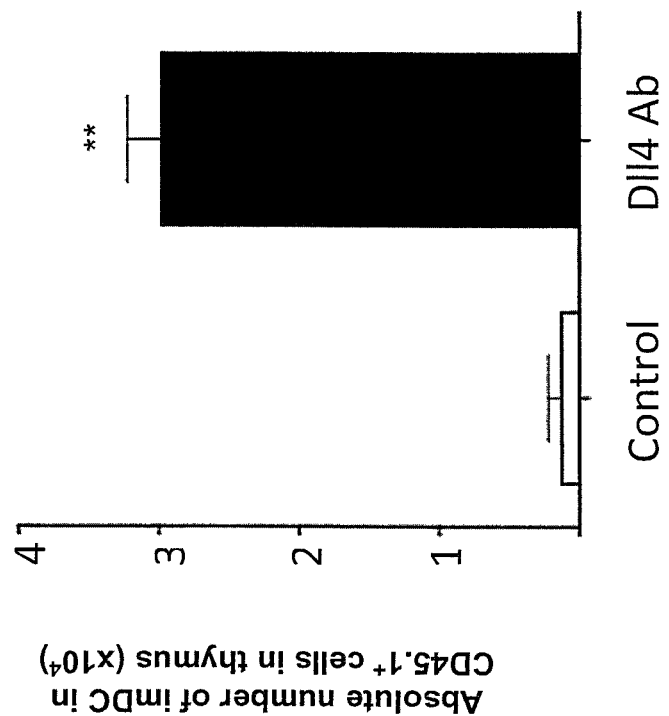
FIG. 4 shows the effect of Dll4 blockade on the development of intra-thymic alternative DC lineage into immature DCs (imDCs) originating from a common T/DC DN1 progenitor. DN1 CD45.1$^+$Lin$^-$ sorted cells were intra-thymically transferred into CD45.2$^+$ host mice treated with Dll4 Ab (■) or hFc control Ab (□).

To examine whether DC expansion could originate from uncommitted T-cell precursors, DN1 CD45.1$^+$Lin$^-$ sorted cells were intra-thymically transferred into CD45.2$^+$ host mice treated with anti-Dll4 Ab. It was found that CD45.1$^+$ cells were accumulated in DN1 stage (data not shown) and immature DCs (imDCs) were detected and expanded in thymus (FIG. 4) ($p<0.01$). No cells were detected in the control Ab-treated mice, possibly because most of DN1-transferred cells were eliminated by T cell negative selection. It was concluded that Dll4 blockade promotes the development of intra-thymic alternative DC lineage originating from a common T/DC DN1 progenitor.

Fms-like tyrosine kinase 3 ligand (Flt3-L) is sufficient and essential for the differentiation of bone marrow progenitors into DCs and the development of peripheral DCs. Serum levels of Flt3-L were unchanged in anti-Dll4 Ab-treated WT animals (data not shown). Furthermore, as shown in Tables 2 and 3 below, the percentages of DC in thymus were expanded in wild-type mice (WT) (Tables 2 and 3), Flt3-L knock-out mice (Flt3-L$^{-/-}$) ($p<0.05$) (Table 2), and Flt3-R knock-out mice (Flt3-R$^{-/-}$) ($p<0.001$) (Table 3), all treated with Dll4 Ab, compared to those treated with control Ab. Thus, Dll4 blockade induces a Flt3-independent DC expansion in thymus.

TABLE 2

| Mice | % DC in Thymus in Mice Treated with: | |
|---|---|---|
| | Control Ab | Dll4 Ab |
| WT | 0.04 ± 0.005 | 0.58 ± 0.13 |
| Flt3-L$^{-/-}$ | 0.04 ± 0.006 | 0.45 ± 0.13 |

TABLE 3

| Mice | % DC in Thymus of Mice Treated with: | |
|---|---|---|
| | Control Ab | Dll4 Ab |
| WT | 0.03 ± 0.003 | 0.37 ± 0.03 |
| Flt3-R$^{-/-}$ | 0.06 ± 0.01 | 0.44 ± 0.02 |

Figure 5:
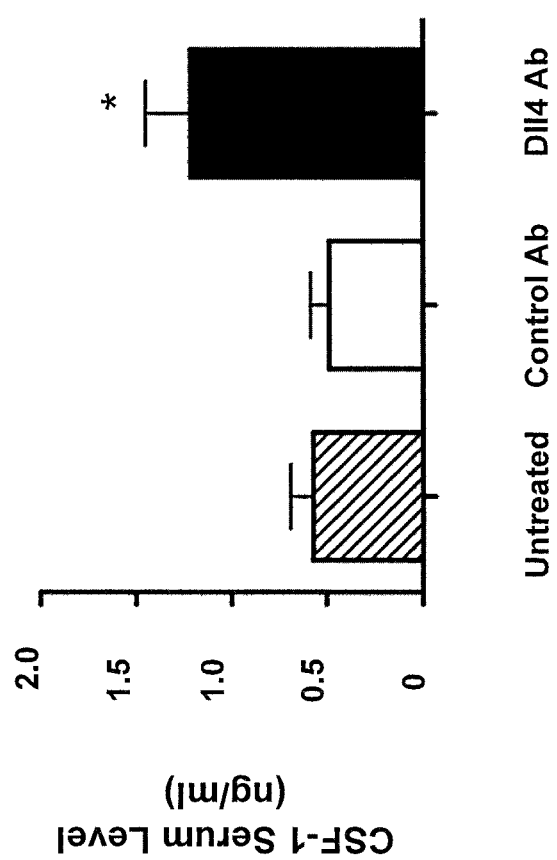
FIG. 5 shows the effect of Dll4 blockage on serum levels of CSF-1 (M-CSF), a key cytokine involved in DC development. Serum CSF-1 levels of mice untreated (▨), or treated with isotype control Ab (□), or Dll4 Ab (■) were measured by enzyme-linked immunosorbent assay (ELISA).

The ability of early T cell progenitors to re-derive towards a non-T cell phenotype has been observed (James P. Di Santo, 2010, *Science* 329:44-45). Gene array analysis was performed in thymocytes and pro-T cells to determine the effect of anti-Dll4 Ab treatment in genes implicated in T versus B and DC cell-lineage specification. It was found that the genes essential for T cell commitment (e.g., Tcf7, Gata3, and Ets1) were downregulated, while genes (Lyl1, Sfpi1) that can each block T cell development, were up-regulated (data not shown; see Di Santo, 2010, supra). Most interestingly, genes controlling DC (PU.1 and Spi-B) and B cell development were also up-regulated (data not shown; see M. Merad et al. 2009, *Bood* 113:3418-3427). In addition, expression of RelB and Id2 as well as interferon regulatory factors (IRFs) 2, 4 and 8-key transcription factors involved in DC subset development were increased (data not shown; see Merad et al. 2009, supra). Finally, gene expression of CSF-1 (M-CSF), a key cytokine involved in DCs development, was found to be up-regulated upon anti-Dll4 Ab treatment ($p<0.05$; data not shown). Furthermore, CSF-1 serum levels were increased upon anti-Dll4 Ab treatment (FIG. 5; $p<0.05$) (see B. Francke, et al. 2008, *Blood* 111:150-159). Thus, it can be concluded that Dll4-Notch signaling blockade down-regulates transcription factors specific for T cell lineage commitment, while up-regulating others crucial in DC development.

Example 2

Effect of Dll4 Deletion on T Cell Development

To evaluate if the effect of Dll4 on DC development observed in Example 1 above was intrinsic to Dll4, DLL4COIN mice, in which Dll4 is conditionally inactivated, were prepared. "Conditional-by-inversion (COIN)" alleles are conditional alleles that rely on an inversible element ("COIN element") to provide recombinase-mediated conditional mutations. DLL4COIN mice contain a tamoxifen-inducible Cre recombinase construct, CreERT2, which encodes a Cre recombinase fused to a mutant estrogen ligand-binding domain (ERT2). CreERT2 is essentially inactive in the absence of tamoxifen and is also not activated by endogenous estrogens. Tamoxifen treatment of the mice will activate CreERT2 and cause the inversion of the COIN element, which abrogates the transcription of all exons downstream of the COIN insertion point, thereby knocking out Dll4. For details of CreERT2 recombinase system, see Feil et al. 1997, *Biochemical and Biophysical Research Communications* 237: 752-757.

DLL4COIN mice (n=6) were injected intraperitoneally (i.p.) with tamoxifen (TAM) (cat #T-5648, Sigma) at 3 mg/150 μl corn oil per mouse three (3) times per week for 2 weeks. DLL4COIN control mice (n=6) were given corn oil without tamoxifen. Likewise, wild type C5B1/6 mice were treated with tamoxifen (n=6) or corn oil only (n=6). Mice were monitored for signs of distress (e.g., fur appearance, low activity, etc.), infections, and excessive loss of body weight. Mice were weighed approximately three times per week. Any mouse that lost more than 20% body weight was removed from the experiment. After 2 weeks of the treatment, thymi were harvested and the thymic cells were analyzed by flow cytometry.

Figure 6:
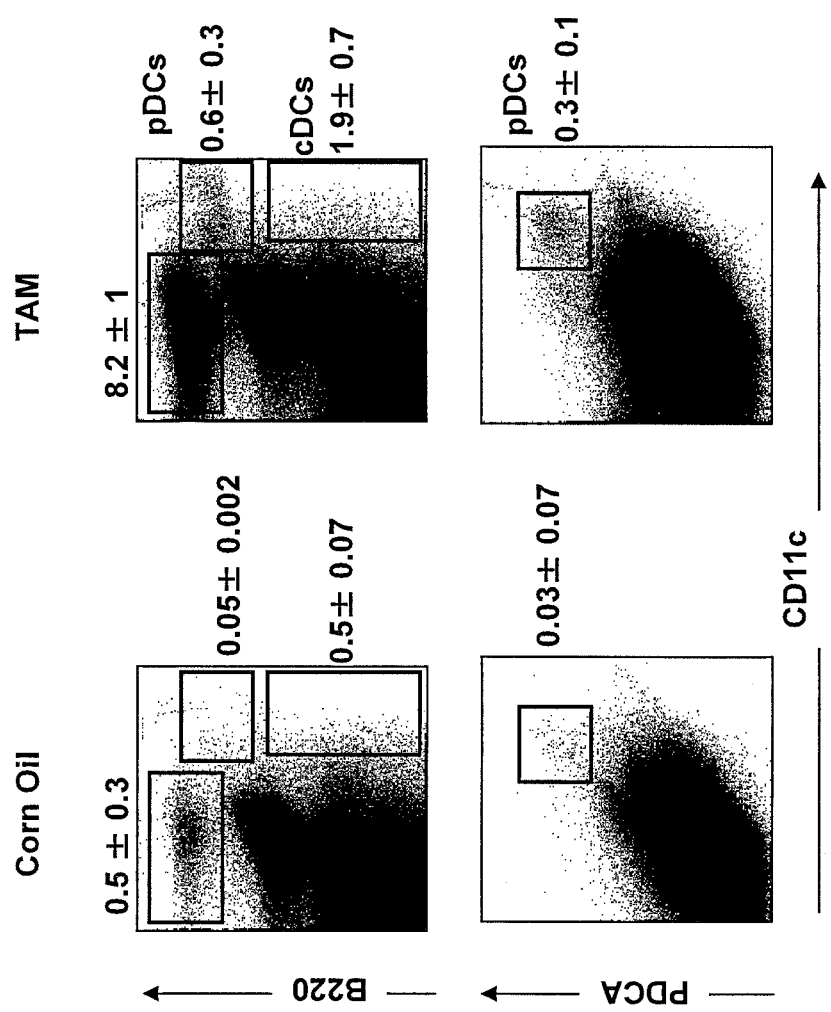
FIG. 6 shows the effects of the genetic Dll4 deletion, upon tamoxifen treatment, on B cell and DC homeostasis in DLL4COIN mice containing a tamoxifen-inducible Cre recombinase construct, CreERT2. Numbers in dot plots represent average percentages (mean±SEM) of B cells and both pDCs and cDCs among total cells in the thymus.

As shown in FIG. 6, in the absence of Dll4 (i.e., in tamoxifen-treated mice), B cells and both pDCs and cDCs were expanded in the thymus, compared to the corn oil-treated mice, indicating that the effects of Dll4 on DC development and homeostasis observed in Example 1 were indeed intrinsic to Dll4. Thus, Dll4-Notch signaling seems to sustain T cell commitment by suppressing non-T cell lineage potential within the pro-T cell population.

Example 3

Effect of Dll4 Blockade or Dll4 Deletion on Tregs Homeostasis

It has been recently shown that Tregs are essential for maintaining normal number of DCs. Upon Treg depletion there is a compensatory Fms-like tyrosine kinase 3 (Flt3)-dependent increase of DCs (Liu et al., 2009, supra). Furthermore, two independent groups showed a feedback control of regulatory T cell homeostasis by DCs in vivo; i.e., increasing the numbers of DCs leads to an increased Treg division and accumulation, which could prevent autoimmune disease development (Darrasse-Jeze G. et al., 2009, *J. Exp. Med.* 206(9):1853-1862; and Swee L K et al., 2009, Blood 113(25): 6277-6287).

Figure 7A:
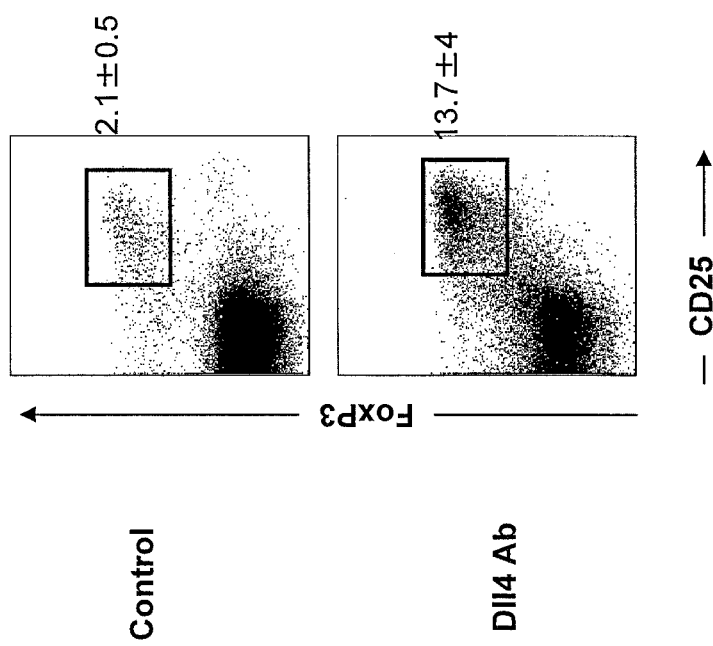
FIG. 7A-7C show the effects of Dll4 blockade/deletion on Treg homeostasis.
Figure 7B:
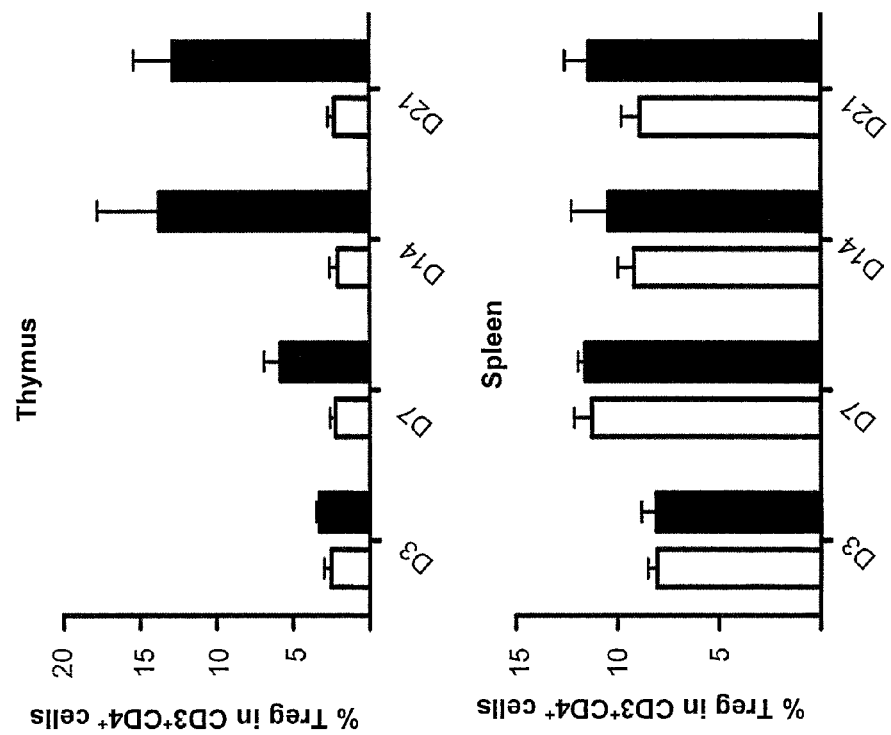

To determine if Dll4 blockade could affect Treg homeostasis, Treg numbers in thymi of the mice treated with the Dll4 Ab or human Fc (control) in Example 1 were measured by flow cytometry. As shown in FIG. 7A, Dll4 blockade resulted in a robust expansion of Tregs within the thymus at day 14 after the initial injection. The expansion of Tregs started at day 7 ($p<0.001$) and reached a maximum effect at day 14 in the thymus ($p<0.001$) after the initial injection (see FIG. 7B), while in the periphery (i.e., spleen) Tregs started appearing only between 14 and 21 days ($p<0.05$) (FIG. 7B and Table 4). In Table 4, fold increases in percentage and absolute number of Tregs in spleen upon treatment with Dll4 Ab, compared to the control mice (hFc-treated), are shown.

TABLE 4

| Days after initial injection | Fold-increase in percentage | Fold-increase in absolute number |
| --- | --- | --- |
| 3 | 1.0 | 1.0 |
| 7 | 1.0 | 1.2 |
| 14 | 1.1 | 1.7 |
| 21 | 1.1 | 1.2 |

Figure 7C:
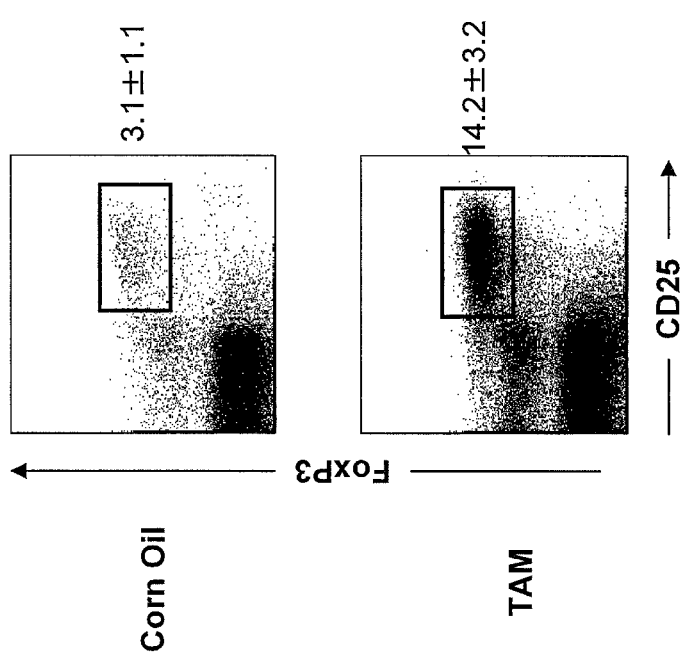

To evaluate if the observed Treg expansion was intrinsic to Dll4 molecule, Treg numbers in thymi of DLL4COIN mice from Example 2 were also measured by flow cytometry. As observed with the Dll4 blockade by Dll4 Ab, conditional inactivation of Dll4 by tamoxifen treatment also resulted in the expansion of Tregs in the thymus, compared to the corn-oil treated mice (see FIG. 7C) as well as wild-type mice treated with tamoxifen (data not shown). Thus, Dll4-Notch signaling sustains DCs and consequently Treg homeostasis and T cell commitment.

Figure 8B:
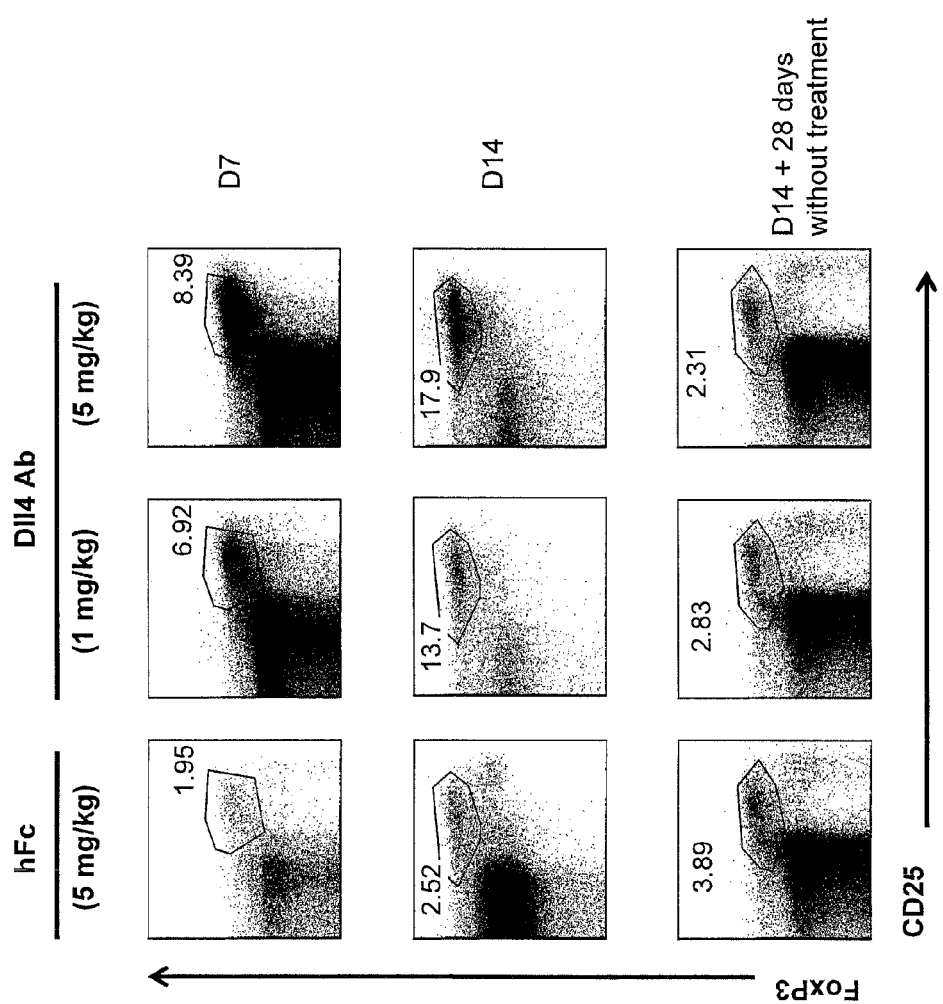

A similar experiment was conducted in mice expressing human Dll4 ("humanized Dll4 mice") using anti-Dll4 Ab (REGN421 having HCVR and LCVR sequences of SEQ ID NO:116 and 118, respectively), which is known to bind an N-terminal-DSL domain of human Dll4. The humanized Dll4 mouse was prepared by replacing the entire extracellular domain of the mouse Dll4 gene with the corresponding extracellular region of the human Dll4 gene (7 kb) in embryonic stem (ES) cells of F1 C57BL/6/129. Homozygous hDll4 mice were generated and bred into C57BL/6 background. Humanized Dll4 mice were treated with 5 mg/kg of hFc (control; n=6), or 1 mg/kg (n=6) or 5 mg/kg (n=6) of REGN421 Ab twice per week for two weeks. Two mice from each treatment group were sacrificed at day 7 and 2 more mice per group were sacrificed at day 14. The thymi were harvested and the cells were stained and examined by flow cytometry. The remaining mice were allowed to recover for additional 4 weeks without any treatment and, at day 28 after the cessation of treatment, they were sacrificed and the thymic cells were analyzed using flow cytometry. After two weeks of treatment, an increase of cDC and pDCs (FIG. 8A) as well as a significant increase in Treg population (FIG. 8B) was observed in the thymus of the anti-Dll4 Ab-treated mice ($p<0.01$). In the thymi of the mice that received Dll4 Ab for 2 weeks, followed by 4 weeks of non-treatment, both DC and Treg numbers returned to the normal level at the end of the period (FIGS. 8A and 8B). Meanwhile, an expansion of DCs and Tregs was also observed in the periphery of Dll4-Ab treated mice, compared to hFc treated mice (data not shown).

Example 4

Effect of Notch Receptor Blockade on Tregs

It has been shown that an expansion of DCs is leading to an expansion of Tregs (Darrasse-Jeze G. et al. 2009). As discussed above, it was observed that upon Dll4 blockade both DCs and Tregs were expanded in the thymus (FIG. 3A and FIG. 7A). In addition, an expansion of both percentages and absolute numbers of DCs and Tregs was also found in the periphery of Dll4-Ab treated mice (Tables 1 and 4). In order to determine if blockade of Notch receptors would lead to the same phenotype as Dll4 deletion, Nicastrin knockout (KO) mice (Nic$^{-/-}$) were studied. Nicastrin is a molecule involved in the Notch signaling pathway and genetic ablation of nicastrin in nicastrin deficient mice results in a blockade of signal transduction downstream of Notch receptors 1, 2, 3 and 4 (Aifantis et al. un-published data). Nicastrin KO mice were shown to exhibit similar phenotype as the Dll4-deleted/blocked mice with an increased number of Tregs, both in percentage and in absolute number, in thymus as well as in spleen (see Table 5).

TABLE 5

| | Thymus | | Spleen | |
| --- | --- | --- | --- | --- |
| Treg | Control mice | Nicastrin KO mice | Control mice | Nicastrin KO mice |
| Treg (%) in CD3$^+$CD4$^+$ cells | 3.3 ± 0.2 | 15.2 ± 2.0 ($p < 0.1$) | 16.0 ± 1.3 | 33.9 ± 2.1 ($p < 0.0001$) |
| Ratio of absolute numbers (Treg/Teff) | 0.04 ± 0.002 | 0.2 ± 0.03 ($p < 0.01$) | 0.2 ± 0.01 | 0.6 ± 0.06 ($p < 0.0001$) |

Finally, when bone marrow cells (BM) from Nic$^{-/-}$ mice were transferred into lethally irradiated WT mice, the expansion of thymic Tregs was observed in Nic$^{-/-}$→WT chimeras, suggesting that such an expansion was a cell-autonomous effect; and Dll4 blockade of the recipient mice with anti-Dll4 Ab had no additive effect (see Table 6).

TABLE 6

| | % Treg in CD3$^+$CD4$^+$ Cells in Recipient WT Mice Treated with: | |
| --- | --- | --- |
| BM Donors | Control Ab | Anti-Dll4 Ab |
| WT | 3.6 ± 0.4 | 35 ± 4 |
| Nic$^{-/-}$ | 37 ± 2 | 41 ± 2 |

These results suggest that interruption of Dll4-Notch signaling by blocking either Dll4 or Notch receptors leads to similar phenotypes with regard to the expansion of Tregs.

To determine if the expansion of Tregs upon Dll4 blockade correlates with DC numbers (Darrasse-Jeze G. et al. 2009, supra), mice lacking DCs were prepared and tested with the Dll4 Ab as in Example 1. Transgenic mice expressing primate diphtheria toxin receptor (DTR) are conferred with diphtheria toxin (DT) sensitivity to their cells, which are DT-insensitive otherwise. DT enters the cells via interaction of its B subunit with the cellular DTR and, upon endocytosis, the DT A subunit is released and catalyzes ADP-ribosylation of elongation factor 2, resulting in the inhibition of protein synthesis followed by rapid apoptosis in both mitotic and terminally differentiated cells. Specificity and timing of cell ablation can be determined by cell type-restricted promoter/enhancer elements and by the regimen of the toxin administration, respectively. To target DT sensitivity to DC, Jung et al. (2002, *Immunity* 17:211-220) have generated mice (CD11cre-DTR mice) that carry a transgene encoding a simian DTR-GFP (green fluorescent protein) fusion protein under the control of the murine CD11c promoter. Since CD11c encodes for all DCs, all murine DC subsets expressing CD11c are deleted upon administration of DT.

Thus-prepared transgenic mice lacking DCs were treated with the Dll4 Ab or hFc control according to the protocol described in Example 1. Fourteen (14) days after the treatment, thymi and spleens were harvested and prepared for analysis. The expression level of Dll4 on the surfaces of specific DC or T cell subsets was evaluated by flow cytometry in order to determine which specific subset the Dll4 Ab bound to. The results showed that DCs and T cells did not express detectable levels of Dll4 on their surface (data not shown). This observation is corroborated by the report that Dll4 is expressed on the surface of thymic epithelial cells (TECs) (Koch et al. 2008, supra). Most importantly, however, it was found that the Dll4 Ab treatment of mice lacking DCs was not able to induce expansion of Treg, while wild-type mice (i.e., DC non-deleted mice) treated with Dll4 Ab significantly increased the proportion of Tregs among $CD3^+CD4^+$ cells ($p<0.001$), suggesting that the expansion of Tregs upon Dll4 Ab treatment was at least in part mediated via DC expansion.

Example 5

Effect of Dll4 Blockade in Experimental Autoimmune Encephalomyelitis (EAE)

$CD4^+CD25^+FoxP3^+$ natural regulatory T cells (i.e., Tregs) play an important role in maintaining self-tolerance and suppress auto-immune diseases, such as type 1 diabetes, autoimmune encephalomyelitis, GVHD and inflammatory bowel disease (IBD) (Darrasse-Jeze G. et al. 2009, supra; Swee L K et al. 2009, supra; and McGreachy et al., 2005, 175(5):3025-3032).

To see if the increased number of Tregs resulted from Dll4 blockade would prevent autoimmune diseases, the impact of Dll4 blockade on an EAE was studied in a mouse model. The EAE mouse model was established by injecting in the footpad of C57Bl/6 mice with myelin oligodendrocyte glycoprotein (MOG) peptide emulsified in complete Freund adjuvant (CFA) followed (24 hours later) by Pertussis toxin (PTX) injection to induce disease. The disease score was determined based on the following symptoms: (0) no symptoms; (1) limp tail; (2) limp tail with hind-leg weakness; (3) partial hind-leg paralysis; (4) complete hind-leg paralysis; (5) paralysis of all limbs; and (6) moribund. Twelve to twenty-four hours prior to the immunization, mice in a pre-induction group (n=10) also received a subcutaneous injection of 25 mg/kg of either anti-Dll4 Ab (REGN577) or isotype control Ab (human antibody specific for CD20, prepared in-house according to the disclosure in US 2008/0260641), or PS/2 (rat/mouse IgG2b against murine integrin-like cellular adhesion molecule VLA-4; ATCC #CRL-1911), while mice in a post-induction group (n=10) received the same on the day the symptoms appeared. PS/2 Ab is known to exacerbate disease relapses and increase the accumulation of $CD4^+$ T cells in the central nervous system in a mouse model for relapsing experimental autoimmune encephalomyelitis (R-EAE) (Theien B E et al., 2001, *J Clin Invest* 107(8):995-1006). The injections of antibodies were conducted twice a week, for two weeks. At the conclusion of the experiment, spinal cords of the mice were carefully removed, crushed and then incubated in a RPMI 1640 medium containing Collagenase D (Sigma Aldrich). EDTA at 2 mM was added to stop the reaction and the mixture was passed through a 70-mm cell strainer and the cell content was analyzed by flow cytometry.

As shown in FIGS. 9A and 9B, the mice treated with isotype control Ab developed symptoms (La, having disease scores more than "0") starting around 10-14 days and peaking between 15 and 21 days, after the MOG injections. In contrast, mice treated with Dll4 Ab were fully prevented from disease progression compared to mice treated with control Ab. Table 7 shows fold-increases in percentage and in absolute number of Tregs in thymus and spleen of the mice treated with Dll4 Ab, compared to mice treated with control Ab.

TABLE 7

| Days after MOG injection | Treg in Thymus | | Treg in Spleen | |
|---|---|---|---|---|
| | Fold-increase in percentage | Fold-increase in absolute number | Fold-increase in percentage | Fold-increase in absolute number |
| 12 | 2.46 | 0.77 | 1.08 | 1.46 |
| 18 | 4.88 | 2.67 | 1.23 | 1.89 |
| 21 | 1.41 | 1.01 | 1.85 | 4.77 |

Tregs seemed to expand primarily within the thymus at around day 18 and a significant expansion was seen in periphery (i.e., spleen) only after day 21.

Under this particular experimental condition, Dll4 Ab treatment at the post-induction stage did not show significant improvement in disease progression. Dosages and/or frequency of Dll4 Ab administrations can be further adjusted within the knowledge of one skilled in the art. Importantly, however, the mice that had received pre-induction Dll4 Ab exhibited a significant decrease in cell infiltration into the spine at day 18, compared to those that had received control Ab (see Table 8 below). Cell infiltration observed in the spinal cord of the mice treated with control Ab could be a major contributor to the disease process in those mice.

As shown in Table 8, there was a 8-fold decrease ($p<0.0001$) in macrophages ($F4/80^+$), a 2.7-fold decrease ($p<0.0001$) in NK cells, 1.7-fold decrease ($p<0.001$) in CD11b cells, and 2.5-fold decrease ($p<0.001$) in B cells in spinal cord of mice treated with Dll4 Ab, compared to the spinal cord of mice treated with control Ab at day 21.

TABLE 8

| Days after MOG injection | Absolute Number of Infiltrating Cells in Spine (×10⁶) | | | | | | | |
|---|---|---|---|---|---|---|---|---|
| | Macrophages | | NK cells | | B cells | | CD11b+ myeloid cells | |
| | Control | Dll4 Ab | Control | Dll4 Ab | Control | Dll4 Ab | Control | Dll4 Ab |
| 12 | 0.4 ± 0.05 | 0.3 ± 0.01 | 0.2 ± 0.03 | 0.1 ± 0.004 | 0.3 ± 0.005 | 0.2 ± 0.006 | 0.9 ± 0.09 | 0.6 ± 0.02 |
| 18 | 1.7 ± 0.5 | 0.2 ± 0.02 | 0.2 ± 0.06 | 0.1 ± 0.005 | 1.8 ± 0.2 | 1.0 ± 0.08 | 4.7 ± 0.7 | 1.8 ± 0.1 |
| 21 | 1.6 ± 0.1 | 0.2 ± 0.01 | 0.8 ± 0.07 | 0.3 ± 0.03 | 1.5 ± 0.1 | 0.6 ± 0.02 | 4.8 ± 0.1 | 2.9 ± 0.2 |

Figure 10:
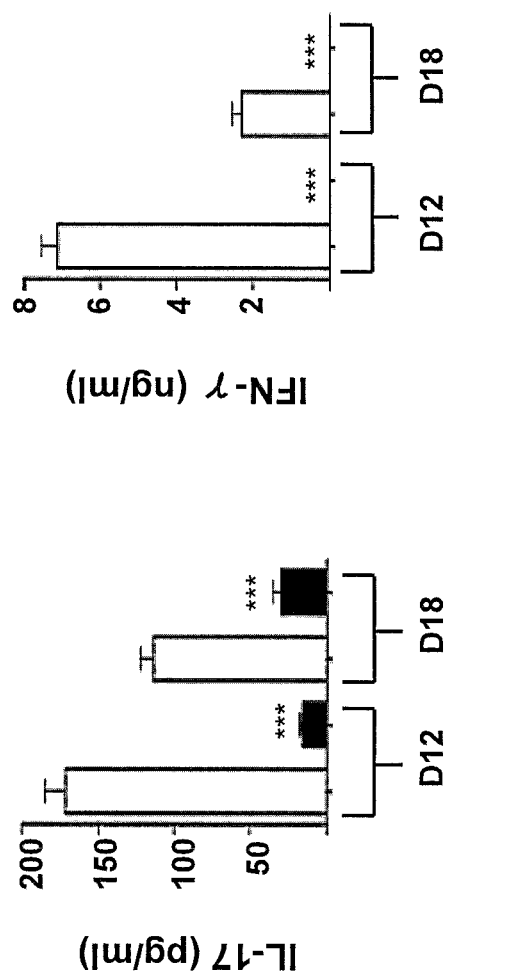
FIG. 10 shows the effects of Dll4 blockade on IL-17 and IFN-γ production in the lymph nodes of EAE mice. The levels of IL-17 (left panel) and IFN-γ (right panel) in the lymph nodes of EAE mice treated with Dll4 Ab (■) or hFc control Ab (□) were measured on days 12 and 18 by ELISA.

Furthermore, production of IL-17 and IFN-γ in lymph nodes in the mice treated with Dll4 Ab was significantly diminished ($p<0.001$) (FIG. 10). Thus, Dll4 could be involved in the pathogenesis of EAE by mediating Th1 development and Dll4 Ab treatment can prevent disease induction by blocking the secretion of Th1 and Th17 cytokines.

Example 6

Effect of Dll4 Blockade on Diabetes

The effect of Dll4 blockade on diabetes was also tested in NOD/ShiLtJ mice ("NOD mice"), a polygenic model for type 1 diabetes (Makino S et al., 1980, *Jikken Dobutsu* 29 (1):1-13; Serreze D V et al., 1997, *J Immunol* 158 (8):3978-86). Diabetes in NOD/ShiLtJ mice is characterized by insulitis and leukocytic infiltration of the pancreatic islets. Marked decreases in pancreatic insulin content occur spontaneously in females at about 12 weeks of age and several weeks later in males. Consequently, plasma glucose levels increase to greater than 250 mg/dL. NOD mice were checked twice a week for blood glucose levels, using a ONETOUCH® mini (LifeScan, Inc.). The mice were considered diabetic after two consecutive readings over 250 mg/dL of blood glucose. The onset of diabetes was dated from the first of the sequential diabetic measurements. The mice were injected with hFc (n=5) or anti-Dll4 Ab (Regn577) (n=10) 25 mg/kg twice per week for 7 weeks starting at 9 weeks of age. Blood glucose levels were monitored once a week with blood samples from the tail.

Figure 11A:
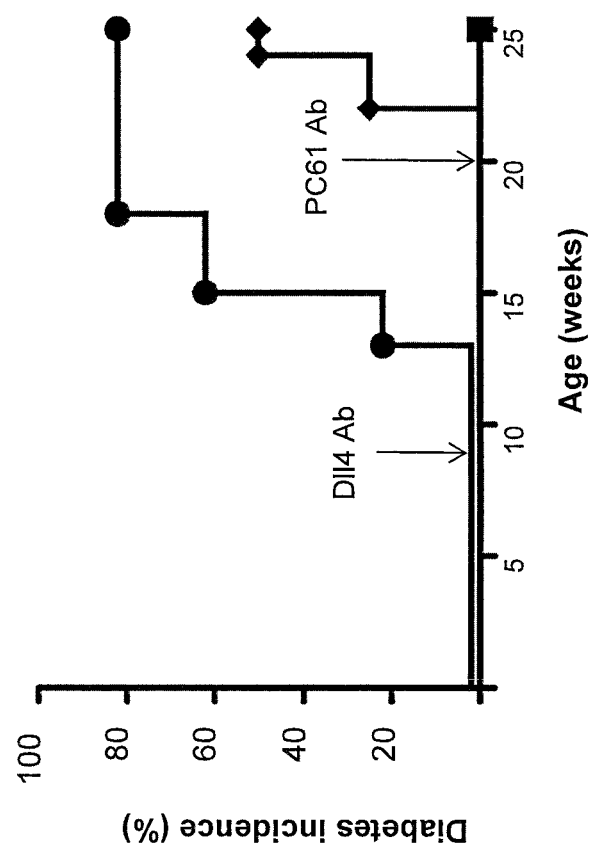

As shown in FIG. 11A, mice treated with hFc started developing spontaneous diabetes with blood glucose levels higher than 250 mg/dL after 13 weeks of age (●). In contrast, mice treated with anti-Dll4 Ab (REGN577) showed no sign of increased glucose level through 25 weeks of age (■) and the measurements are continuing for additional 10 weeks. Dll4-Ab treatment before the diabetes onset prevented the development of diabetes and the treated animals did not seem to ever develop diabetes. Interestingly, when 5 out of 10 mice treated with Dll4 Ab were injected with anti-CD25 (PC61) mAb at 20 weeks of age in order to deplete the Tregs (♦), their blood glucose levels started increasing 1-2 weeks later and the mice became diabetic. This indicated that the preventive effect of Dll4 Ab on type I diabetes was mediated, at least in part, by Tregs (FIG. 11A).

Figure 11B:
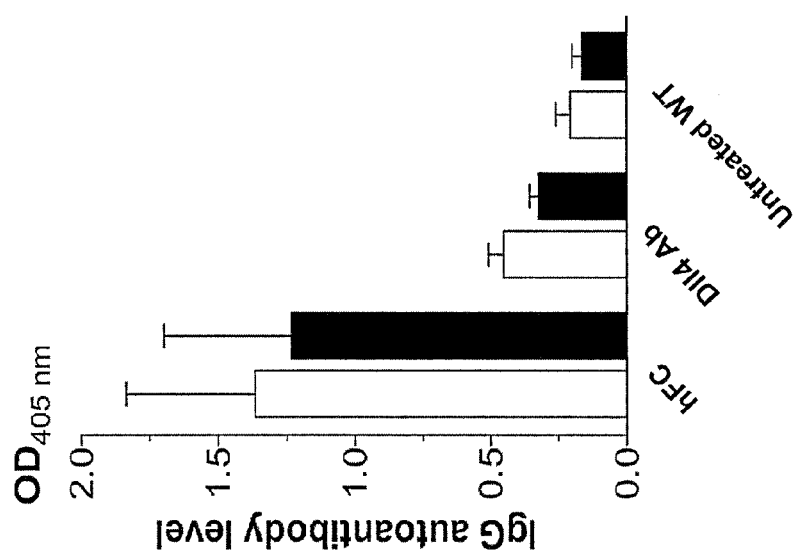

Insulin and GAD65 are two standard auto-antibodies that are found in the sera of diabetic NOD mice as well as of diabetic individuals. Accordingly, the serum levels of auto-antibodies in the mice treated with hFc control or Dll4 Ab were measured by ELISA. As shown in FIG. 11B, Dll4-Ab treatment blocked the production of anti-Insulin (□) and anti-GAD65 (■) auto-antibodies at levels similar to those of untreated WT C57Bl/6 (i.e., non-NOD mice; negative control animals). In contrast, NOD (diabetic) mice that received hFc control had high levels of auto-antibodies in their sera. In addition, when the pancreas sections of 23-week old mice, which had been treated with Dll4 Ab and showing no diabetic symptoms, were stained with H&E (Hematoxylin and Eosin), normal numbers of pancreatic islets (the cells that produce insulin or glucagon and their destruction is directly correlated with diabetes incidence) with preserved morphology were observed (FIG. 11C, left panel, and FIG. 11D, left panel). Further, no cellular infiltration within the islets was observed with Dll4 Ab-treated mice (FIG. 11C, left panel, and FIG. 11D, right panel). In contrast, diabetic animals, which had been treated with hFc control, had significantly lower numbers of pancreatic islets (FIG. 11C, right panel, and FIG. 11D, left panel) in their pancreas than the Dll4 Ab-treated mice and the remaining very few islets contained high levels of cellular infiltration (FIG. 11C, right panel, and FIG. 11D, right panel). Thus, Dll4 Ab was able to prevent diabetes completely for a prolonged period and its effect seemed to be, at least in part, mediated by the expansion of Tregs; however, it is possible that an additional mechanism(s) may be involved in the protective effect of Dll4 Ab on pancreatic islets and/or insulin.

Figure 11E:
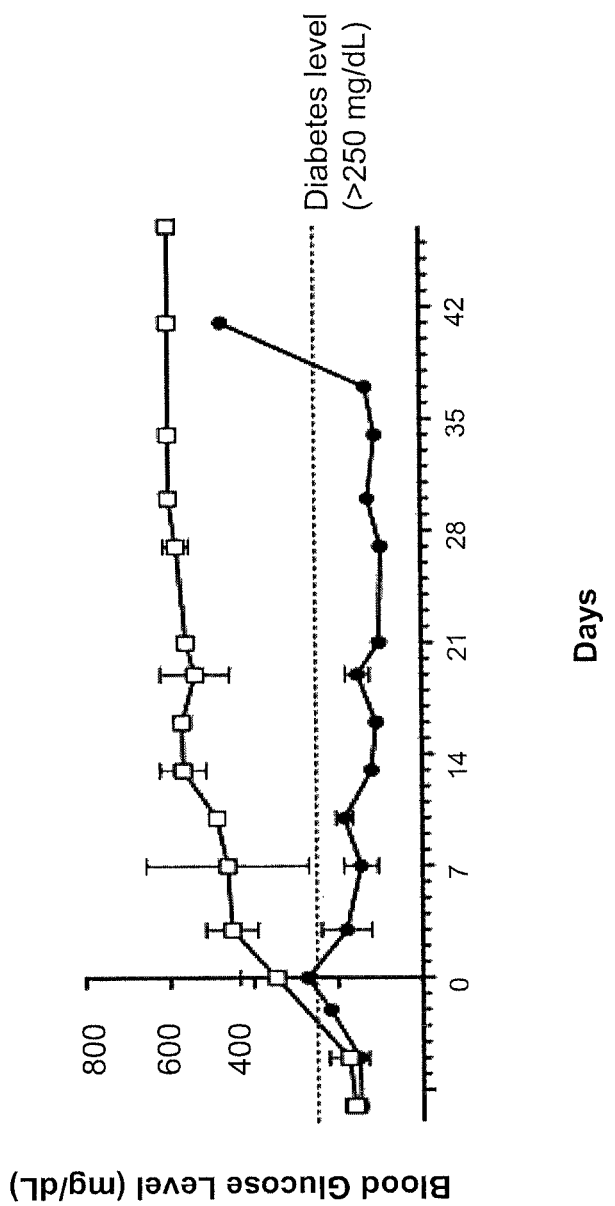

Actual blood glucose levels of the diabetic mice treated with Dll4 Ab were determined and compared with those of the mice treated with hFc control. Diabetic mice were treated with 25 mg/kg of Dll4 Ab (n=3) or control hFc (n=4) at the onset of disease (day 0). Upon Dll4 Ab treatment, diabetic mice significantly decreased the glucose level from about 350 mg/dL to a normal level (about 120-130 mg/dL) (FIG. 11E). This effect lasted for an average of 4 to 5 weeks. In general, it was further observed that, when diabetic mice having less than 350 mg/dL of blood glucose was treated with Dll4 Ab, their glucose levels dropped to the normal level and this effect lasted longer than those having more than 350 mg/dL of blood glucose at the time of treatment. This indicates that there is a certain window of opportunity for a prolonged and effective treatment for controlling blood glucose levels with Dll4 Ab. Thus, without being bound by any specific mechanisms described herein, these observations suggest that Dll4 antibodies have a great therapeutic potential for type I diabetes.

The results from the experiments above have revealed an existence of a previously unknown regulatory loop that controls the numbers of Treg cells and DCs in vivo. This regulatory circuit is likely to be essential to the balance between immunity and tolerance, but most importantly makes, for the first time, the link between three important components of the immune system, i.e., Dll4-DCs-Tregs. Thus, a therapy with Dll4 antagonists presents an effective methodology to control Treg numbers in vivo and consequently control the progression of autoimmune diseases and related conditions.

The invention claimed is:

1. A method of lowering blood glucose levels, comprising administering to a subject diagnosed with diabetes mellitus type I a therapeutically effective amount of an anti-Dll4 antibody or fragment thereof that binds human Dll4 and blocks an interaction between Dll4 and a Notch receptor, wherein the antibody or fragment thereof comprises a heavy chain variable region (HCVR) comprising heavy chain CDR1, CDR2 and CDR3 sequences of SEQ ID NO:22, 24 and 26, respectively, and a light chain variable region (LCVR) comprising light chain CDR1, CDR2 and CDR3 sequences of SEQ ID NO:30, 32 and 34, respectively.

2. The method of claim 1, wherein the antibody or fragment thereof comprises (a) a HCVR sequence of SEQ ID NO:20 or 116, and a LCVR sequence of SEQ ID NO:28 or 118, or (b) a HCVR/LCVR combination of SEQ ID NO:20/28 or 116/118.

3. The method of claim 1, further comprising coadministering concurrently or sequentially with the anti-Dll4 antibody or fragment thereof a therapeutically effective amount of at least one additional blood glucose lowering agent.

4. The method of claim 3, wherein the additional blood glucose lowering agent is insulin or an analogue thereof.

5. The method of claim 2, wherein the antibody or fragment thereof comprises a HCVR/LCVR combination of SEQ ID NO: 20/28.

6. The method of claim 2, wherein the antibody or fragment thereof comprises a HCVR/LCVR combination of SEQ ID NO: 116/118.

* * * * *

SEQUENCE LISTING

<160> NUMBER OF SEQ ID NOS: 118

<210> SEQ ID NO 1
<211> LENGTH: 2058
<212> TYPE: DNA
<213> ORGANISM: Homo sapiens

<400> SEQUENCE: 1

| | | | | | | |
|---|---|---|---|---|---|---|
| atggcggcag | cgtcccggag | cgcctctggc | tgggcgctac | tgctgctggt | ggcactttgg | 60 |
| cagcagcgcg | cggccggctc | cggcgtcttc | cagctgcagc | tgcaggagtt | catcaacgag | 120 |
| cgcggcgtac | tggccagtgg | gcggccttgc | gagcccggct | gccggacttt | cttccgcgtc | 180 |
| tgccttaagc | acttccaggc | ggtcgtctcg | cccggaccct | gcaccttcgg | gaccgtctcc | 240 |
| acgccggtat | tgggcaccaa | ctccttcgct | gtccgggacg | acagtagcgg | cggggggcgc | 300 |
| aaccctctcc | aactgccctt | caatttcacc | tggccgggta | ccttctcgct | catcatcgaa | 360 |
| gcttggcacg | cgccaggaga | cgacctgcgg | ccagaggcct | gccaccaga | tgcactcatc | 420 |
| agcaagatcg | ccatccaggg | ctccctagct | gtgggtcaga | actggttatt | ggatgagcaa | 480 |
| accagcaccc | tcacaaggct | gcgctactct | taccgggtca | tctgcagtga | caactactat | 540 |
| ggagacaact | gctcccgcct | gtgcaagaag | cgcaatgacc | acttcggcca | ctatgtgtgc | 600 |
| cagccagatg | gcaacttgtc | ctgcctgccc | ggttggactg | ggaatattg | ccaacagcct | 660 |
| atctgtcttt | cgggctgtca | tgaacagaat | ggctactgca | gcaagccagc | agagtgcctc | 720 |
| tgccgcccag | gctggcaggg | ccggctgtgt | aacgaatgca | tcccccacaa | tggctgtcgc | 780 |
| cacggcacct | gcagcactcc | ctggcaatgt | acttgtgatg | agggctgggg | aggcctgttt | 840 |
| tgtgaccaag | atctcaacta | ctgcacccac | cactccccat | gcaagaatgg | ggcaacgtgc | 900 |
| tccaacagtg | ggcagcgaag | ctacacctgc | acctgtcgcc | caggctacac | tggtgtggac | 960 |
| tgtgagctgg | agctcagcga | gtgtgacagc | aaccccgtc | gcaatggagg | cagctgtaag | 1020 |
| gaccaggagg | atggctacca | ctgcctgtgt | cctccgggct | actatggcct | gcattgtgaa | 1080 |
| cacagcacct | tgagctgcgc | cgactccccc | tgcttcaatg | gggctcctg | ccgggagcgc | 1140 |
| aaccagggg | ccaactatgc | ttgtgaatgt | cccccaact | tcaccggctc | caactgcgag | 1200 |
| aagaaagtgg | acaggtgcac | cagcaacccc | tgtgccaacg | ggggacagtg | cctgaaccga | 1260 |
| ggtccaagcc | gcatgtgccg | ctgccgtcct | ggattcacgg | gcacctactg | tgaactccac | 1320 |
| gtcagcgact | gtgcccgtaa | cccttgcgcc | cacggtggca | cttgccatga | cctggagaat | 1380 |
| gggctcatgt | gcacctgccc | tgccggcttc | tctggccgac | gctgtgaggt | gcggacatcc | 1440 |
| atcgatgcct | gtgcctcgag | tccctgcttc | aacagggcca | cctgctacac | cgacctctcc | 1500 |
| acagacacct | tgtgtgcaa | ctgcccttat | ggctttgtgg | gcagccgctg | cgagttcccc | 1560 |
| gtgggcttgc | cgcccagctt | ccctggggtg | ccgtctcgc | tgggtgtggg | gctggcagtg | 1620 |
| ctgctggtac | tgctgggcat | ggtggcagtg | gctgtgcggc | agctgcggct | tcgacggccg | 1680 |
| gacgacggca | gcagggaagc | catgaacaac | ttgtcggact | tccagaagga | caacctgatt | 1740 |
| cctgccgccc | agcttaaaaa | cacaaaccag | aagaaggagc | tggaagtgga | ctgtggcctg | 1800 |
| gacaagtcca | actgtggcaa | acagcaaaac | cacacattgg | actataatct | ggccccaggg | 1860 |
| cccctggggc | ggggaccat | gccaggaaag | tttccccaca | gtgacaagag | cttaggagag | 1920 |
| aaggcgccac | tgcggttaca | cagtgaaaag | ccagagtgtc | ggatatcagc | gatatgctcc | 1980 |
| cccagggact | ccatgtacca | gtctgtgtgt | ttgatatcag | aggagaggaa | tgaatgtgtc | 2040 |
| attgccacgg | aggtataa | | | | | 2058 |

<210> SEQ ID NO 2
<211> LENGTH: 685
<212> TYPE: PRT
<213> ORGANISM: Homo sapiens

<400> SEQUENCE: 2

```
Met Ala Ala Ser Arg Ser Ala Ser Gly Trp Ala Leu Leu Leu Leu
  1               5                  10                  15

Val Ala Leu Trp Gln Gln Arg Ala Ala Gly Ser Gly Val Phe Gln Leu
             20                  25                  30

Gln Leu Gln Glu Phe Ile Asn Glu Arg Gly Val Leu Ala Ser Gly Arg
         35                  40                  45

Pro Cys Glu Pro Gly Cys Arg Thr Phe Phe Arg Val Cys Leu Lys His
     50                  55                  60

Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
```

```
              370                 375                 380
Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 3
<211> LENGTH: 372
<212> TYPE: DNA
<213> ORGANISM: Artificial Sequence
<220> FEATURE:
<223> OTHER INFORMATION: Synthetic

<400> SEQUENCE: 3
caggtgcagc tggtgcagtc aggtccagga ctggtgaagc cctcgcagaa cctctcactc      60
acctgtgcca tctccggaga cagtgtctct agtgatagtg ctgcttggaa ctggatcagg     120
cagtccccat cgagaggcct tgagtggctg gaaggacat actacaggtc caagtggtat      180
aatgattatg cagtatctgt gaaaagtcga ataaccttca acccagatac atccaagaac     240
cacatctccc tgcagctgaa ctctgtgact cccgaggaca cggctatcta ttactgtgca     300
```

```
agagaggggg ataattggaa ttacggctgg ctcgacccct ggggccaggg aaccacggtc    360
accgtctcct ca                                                        372
```

<210> SEQ ID NO 4
<211> LENGTH: 124
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Gln Ser Gly Pro Gly Leu Val Lys Pro Ser Gln
1               5                   10                  15

Asn Leu Ser Leu Thr Cys Ala Ile Ser Gly Asp Ser Val Ser Ser Asp
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Phe Asn Pro Asp Thr Ser Lys Asn
65                  70                  75                  80

His Ile Ser Leu Gln Leu Asn Ser Val Thr Pro Glu Asp Thr Ala Ile
                85                  90                  95

Tyr Tyr Cys Ala Arg Glu Gly Asp Asn Trp Asn Tyr Gly Trp Leu Asp
            100                 105                 110

Pro Trp Gly Gln Gly Thr Thr Val Thr Val Ser Ser
        115                 120

<210> SEQ ID NO 5
<211> LENGTH: 30
<212> TYPE: DNA
<213> ORGANISM: Artificial Sequence
<220> FEATURE:
<223> OTHER INFORMATION: Synthetic

<400> SEQUENCE: 5

```
ggagacagtg tctctagtga tagtgctgct                                     30
```

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gly Asp Ser Val Ser Ser Asp Ser Ala Ala
1               5                   10

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7

```
acatactaca ggtccaagtg gtataat                                        27
```

<210> SEQ ID NO 8
<211> LENGTH: 9
<212> TYPE: PRT

```
<213> ORGANISM: Artificial Sequence
<220> FEATURE:
<223> OTHER INFORMATION: Synthetic

<400> SEQUENCE: 8

Thr Tyr Tyr Arg Ser Lys Trp Tyr Asn
 1               5

<210> SEQ ID NO 9
<211> LENGTH: 42
<212> TYPE: DNA
<213> ORGANISM: Artificial Sequence
<220> FEATURE:
<223> OTHER INFORMATION: Synthetic

<400> SEQUENCE: 9
gcaagagagg gggataattg gaattacggc tggctcgacc cc                         42

<210> SEQ ID NO 10
<211> LENGTH: 14
<212> TYPE: PRT
<213> ORGANISM: Artificial Sequence
<220> FEATURE:
<223> OTHER INFORMATION: Synthetic

<400> SEQUENCE: 10

Ala Arg Glu Gly Asp Asn Trp Asn Tyr Gly Trp Leu Asp Pro
 1               5                  10

<210> SEQ ID NO 11
<211> LENGTH: 336
<212> TYPE: DNA
<213> ORGANISM: Artificial Sequence
<220> FEATURE:
<223> OTHER INFORMATION: Synthetic

<400> SEQUENCE: 11
gacatccagt tgacccagtc tccactctcc ctgcccgtca cccctggaga gccggcctcc      60
atctcctgca ggtctagtca gagcctcctt cttagtaatg gatacaacta tttggattgg    120
tacctgcaga agccagggca gtctccacaa ctcctgatct atttggtttc tagtcgggcc    180
tccggggtcc ctgacaggtt cagtggcagt ggatccggca cagattttac actgaaaatc    240
agcagagtgg aggctgagga ttttggaatt tattattgta tgcaagctct acaaactccg    300
tacacttttg gccgggggac caaggtggaa atcaaa                              336

<210> SEQ ID NO 12
<211> LENGTH: 112
<212> TYPE: PRT
<213> ORGANISM: Artificial Sequence
<220> FEATURE:
<223> OTHER INFORMATION: Synthetic

<400> SEQUENCE: 12

Asp Ile Gln Leu Thr Gln Ser Pro Leu Ser Leu Pro Val Thr Pro Gly
 1               5                  10                  15

Glu Pro Ala Ser Ile Ser Cys Arg Ser Ser Gln Ser Leu Leu Leu Ser
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Val Ser Ser Arg Ala Ser Gly Val Pro
     50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Phe Gly Ile Tyr Tyr Cys Met Gln Ala
                    85                  90                  95

Leu Gln Thr Pro Tyr Thr Phe Gly Arg Gly Thr Lys Val Glu Ile Lys
            100                 105                 110
```

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
cagagcctcc ttcttagtaa tggatacaac tat                              33

<210> SEQ ID NO 14
<211> LENGTH: 11
<212> TYPE: PRT
<213> ORGANISM: Artificial Sequence
<220> FEATURE:
<223> OTHER INFORMATION: Synthetic

<400> SEQUENCE: 14

```
Gln Ser Leu Leu Leu Ser Asn Gly Tyr Asn Tyr
 1               5                  10
```

<210> SEQ ID NO 15
<211> LENGTH: 9
<212> TYPE: DNA
<213> ORGANISM: Artificial Sequence
<220> FEATURE:
<223> OTHER INFORMATION: Synthetic

<400> SEQUENCE: 15 ttggtttct                                                          9

<210> SEQ ID NO 16
<211> LENGTH: 3
<212> TYPE: PRT
<213> ORGANISM: Artificial Sequence
<220> FEATURE:
<223> OTHER INFORMATION: Synthetic

<400> SEQUENCE: 16

```
Leu Val Ser
 1
```

<210> SEQ ID NO 17
<211> LENGTH: 27
<212> TYPE: DNA
<213> ORGANISM: Artificial Sequence
<220> FEATURE:
<223> OTHER INFORMATION: Synthetic

<400> SEQUENCE: 17
atgcaagctc tacaaactcc gtacact                                     27

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Met Gln Ala Leu Gln Thr Pro Tyr Thr
 1               5

<210> SEQ ID NO 19
<211> LENGTH: 369
<212> TYPE: DNA
<213> ORGANISM: Artificial Sequence
<220> FEATURE:
<223> OTHER INFORMATION: Synthetic

<400> SEQUENCE: 19
gaggtgcagc tggtgcagtc tgggggaggc gtggtccagc ctggggaggtc cctgagactc     60 tcctgtgcag cgtctggatt caccttcagt agttatggca tgcactgggt ccgccaggct    120
ccaggcaagg gctggagtg gtgtcattt ttatggtatg atggaactaa taaaaactat    180
gtagagtccg tgaagggccg attcaccatc tcaagagaca attccaagaa tatgctgtat    240
ctggaaatga acagcctgag agccgaggac acggctgtgt attactgtgc gagagatcac    300
gattttagga gtggttatga ggggtggttc gaccctggg gccagggaac cctggtcacc    360
gtctcctca                                                            369

<210> SEQ ID NO 20
<211> LENGTH: 123
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Gln Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Phe Leu Trp Tyr Asp Gly Thr Asn Lys Asn Tyr Val Glu Ser Val
    50                  55                  60

Lys Gly Arg Phe Thr Ile Ser Arg Asp Asn Ser Lys Asn Met Leu Tyr
65                  70                  75                  80

Leu Glu Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggattcacct tcagtagtta tggc                                            24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe Ser Ser Tyr Gly
1               5

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23
ttatggtatg atggaactaa taaa                                          24

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Leu Trp Tyr Asp Gly Thr Asn Lys
1               5

<210> SEQ ID NO 25
<211> LENGTH: 48
<212> TYPE: DNA
<213> ORGANISM: Artificial Sequence
<220> FEATURE:
<223> OTHER INFORMATION: Synthetic

<400> SEQUENCE: 25
gcgagagatc acgattttag gagtggttat gagggGtggt tcgacccc              48

<210> SEQ ID NO 26
<211> LENGTH: 16
<212> TYPE: PRT
<213> ORGANISM: Artificial Sequence
<220> FEATURE:
<223> OTHER INFORMATION: Synthetic

<400> SEQUENCE: 26

Ala Arg Asp His Asp Phe Arg Ser Gly Tyr Glu Gly Trp Phe Asp Pro
1               5                   10                  15

<210> SEQ ID NO 27
<211> LENGTH: 321
<212> TYPE: DNA
<213> ORGANISM: Artificial Sequence
<220> FEATURE:
<223> OTHER INFORMATION: Synthetic

<400> SEQUENCE: 27
gaaatagtga tgacacagtc tccagccacc ctgtctttgt ctccagggga aagagccacc   60
ctctcctgca gggccagtca gagtgttagc agctacttag cctggtacca acagaaacct  120
ggccaggctc ccaggctcct catctatgat gcatccaaca gggccactgg catcccagcc  180
aggttcagtg gcagtgggtc tgggacagac ttcactctca ccatcagcag cctagagcct  240
gaagattttg cagtttatta ctgtcaacac cgtagcaact ggcctccac tttcggcgga  300 gggaccaagg tggaaatcaa a                                            321

<210> SEQ ID NO 28
<211> LENGTH: 107
<212> TYPE: PRT
<213> ORGANISM: Artificial Sequence
<220> FEATURE:
<223> OTHER INFORMATION: Synthetic

<400> SEQUENCE: 28

```
Glu Ile Val Met Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln His Arg Ser Asn Trp Pro Pro
                 85                  90                  95

Thr Phe Gly Gly Gly Thr Lys Val Glu Ile Lys
            100                 105
```

<210> SEQ ID NO 29
<211> LENGTH: 18
<212> TYPE: DNA
<213> ORGANISM: Artificial Sequence
<220> FEATURE:
<223> OTHER INFORMATION: Synthetic

<400> SEQUENCE: 29
cagagtgtta gcagctac                                                 18

<210> SEQ ID NO 30
<211> LENGTH: 6
<212> TYPE: PRT
<213> ORGANISM: Artificial Sequence
<220> FEATURE:
<223> OTHER INFORMATION: Synthetic

<400> SEQUENCE: 30

```
Gln Ser Val Ser Ser Tyr
  1               5
```

<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31 gatgcatcc                                                            9

<210> SEQ ID NO 32
<211> LENGTH: 3
<212> TYPE: PRT
<213> ORGANISM: Artificial Sequence
<220> FEATURE:
<223> OTHER INFORMATION: Synthetic

<400> SEQUENCE: 32

Asp Ala Ser
 1

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
caacaccgta gcaactggcc tcccact                                          27

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln His Arg Ser Asn Trp Pro Pro Thr
 1               5

<210> SEQ ID NO 35
<211> LENGTH: 357
<212> TYPE: DNA
<213> ORGANISM: Artificial Sequence
<220> FEATURE:
<223> OTHER INFORMATION: Synthetic

<400> SEQUENCE: 35
caggtgcagc tgcaggagtc gggcccagga ctggtgaagc cttcacagac cctgtccctc      60
acctgcactg tctctgatgg ctccatcaac agtgttgaat cctactggac ctggatccgc     120
cagcacccag ggaagggcct ggagtggatt ggatacatca aatacactgg gggcatccac     180
tataacccgt ccctcaagag tcgacttgcc atatcagtgg acacgtcaaa gaaccagttc     240
tccctgaaaa tgagctctgt gactgccgcg gacacggccg tgtattactg tgcgagagca     300
cgtggaagtc atacttttga tgtctggggc caggggacaa tggtcaccgt ctcttca        357

<210> SEQ ID NO 36
<211> LENGTH: 119
<212> TYPE: PRT
<213> ORGANISM: Artificial Sequence
<220> FEATURE:
<223> OTHER INFORMATION: Synthetic

<400> SEQUENCE: 36

Gln Val Gln Leu Gln Glu Ser Gly Pro Gly Leu Val Lys Pro Ser Gln
 1               5                  10                  15

Thr Leu Ser Leu Thr Cys Thr Val Ser Asp Gly Ser Ile Asn Ser Val
                20                  25                  30

Glu Ser Tyr Trp Thr Trp Ile Arg Gln His Pro Gly Lys Gly Leu Glu
            35                  40                  45

Trp Ile Gly Tyr Ile Lys Tyr Thr Gly Gly Ile His Tyr Asn Pro Ser
        50                  55                  60

Leu Lys Ser Arg Leu Ala Ile Ser Val Asp Thr Ser Lys Asn Gln Phe
 65                  70                  75                  80

Ser Leu Lys Met Ser Ser Val Thr Ala Ala Asp Thr Ala Val Tyr Tyr
                85                  90                  95

Cys Ala Arg Ala Arg Gly Ser His Thr Phe Asp Val Trp Gly Gln Gly

Thr Met Val Thr Val Ser Ser
115

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
gatggctcca tcaacagtgt tgaatcctac            30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Asp Gly Ser Ile Asn Ser Val Glu Ser Tyr
1               5                   10

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39
atcaaataca ctgggggcat c            21

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Ile Lys Tyr Thr Gly Gly Ile
1               5

<210> SEQ ID NO 41
<211> LENGTH: 33
<212> TYPE: DNA
<213> ORGANISM: Artificial Sequence
<220> FEATURE:
<223> OTHER INFORMATION: Synthetic

<400> SEQUENCE: 41
gcgagagcac gtggaagtca tactttgat gtc            33

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42

Ala Arg Ala Arg Gly Ser His Thr Phe Asp Val
1               5                   10

<210> SEQ ID NO 43
<211> LENGTH: 324
<212> TYPE: DNA
<213> ORGANISM: Artificial Sequence
<220> FEATURE:
<223> OTHER INFORMATION: Synthetic

<400> SEQUENCE: 43

```
gaaattgtgc tgactcagtc tccaggcacc ctgtcttggt ctccagggga aagagccacc      60
ctctcctgca gggccagtca gagtattagc agtaactact tagcctggta ccagcagaaa     120
cctggccagg ctcccagact cctcatttat ggtgcatcca gcagggtcac tggcatccca     180
gacaggttca gtggcagtgg gtctgggaca gacttcactc tcaccatcag cagactggag     240
cctgaagatt ttgcactgta ttattgtcag cagtatagta ggtcaccgat caccttcggc     300
caagggacca agtggatat caaa                                             324
```

<210> SEQ ID NO 44
<211> LENGTH: 108
<212> TYPE: PRT
<213> ORGANISM: Artificial Sequence
<220> FEATURE:
<223> OTHER INFORMATION: Synthetic

<400> SEQUENCE: 44

```
Glu Ile Val Leu Thr Gln Ser Pro Gly Thr Leu Ser Trp Ser Pro Gly
 1               5                  10                  15

Glu Arg Ala Thr Leu Ser Cys Arg Ala Ser Gln Ser Ile Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln Gln Tyr Ser Arg Ser Pro
                85                  90                  95

Ile Thr Phe Gly Gln Gly Thr Lys Val Asp Ile Lys
            100                 105
```

<210> SEQ ID NO 45
<211> LENGTH: 21
<212> TYPE: DNA
<213> ORGANISM: Artificial Sequence
<220> FEATURE:
<223> OTHER INFORMATION: Synthetic

<400> SEQUENCE: 45

```
cagagtatta gcagtaacta c                                                21
```

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

```
Gln Ser Ile Ser Ser Asn Tyr
 1               5
```

<210> SEQ ID NO 47
<211> LENGTH: 9
<212> TYPE: DNA
<213> ORGANISM: Artificial Sequence
<220> FEATURE:
<223> OTHER INFORMATION: Synthetic

<400> SEQUENCE: 47 ggtgcatcc                                                                                      9

<210> SEQ ID NO 48
<211> LENGTH: 3
<212> TYPE: PRT
<213> ORGANISM: Artificial Sequence
<220> FEATURE:
<223> OTHER INFORMATION: Synthetic

<400> SEQUENCE: 48

Gly Ala Ser
 1

<210> SEQ ID NO 49
<211> LENGTH: 27
<212> TYPE: DNA
<213> ORGANISM: Artificial Sequence
<220> FEATURE:
<223> OTHER INFORMATION: Synthetic

<400> SEQUENCE: 49
cagcagtata gtaggtcacc gatcacc                                                                 27

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Gln Gln Tyr Ser Arg Ser Pro Ile Thr
 1               5

<210> SEQ ID NO 51
<211> LENGTH: 357
<212> TYPE: DNA
<213> ORGANISM: Artificial Sequence
<220> FEATURE:
<223> OTHER INFORMATION: Synthetic

<400> SEQUENCE: 51
caggtgcagc tgcaggagtc gggcccagga ctggtgaagc cttcacagac cctgtccctc          60
acctgcactg tctctggtgg ctccatcaac agtgttactt actactggac ctggatccgc         120
cagcacccag ggaggggcct agagtggatt gggtacatca aattcagtgg gagcacctac         180
tacaacccgt ccctcaaggg tcgagtcacc atatcagtgg acacgtctaa gaaccaattc         240
tcccttaaaa ttaactctgt gactgccgcg gacacggccg tgttttactg tgcgagagct         300
tctggaagtc atactttga tatctggggc caagggacaa tggtcaccgt ctcctca            357

<210> SEQ ID NO 52
<211> LENGTH: 119
<212> TYPE: PRT
<213> ORGANISM: Artificial Sequence
<220> FEATURE:
<223> OTHER INFORMATION: Synthetic

<400> SEQUENCE: 52

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Val
            20                  25                  30

Thr Tyr Tyr Trp Thr Trp Ile Arg Gln His Pro Gly Arg Gly Leu Glu
        35                  40                  45

Trp Ile Gly Tyr Ile Lys Phe Ser Gly Ser Thr Tyr Tyr Asn Pro Ser
    50                  55                  60

Leu Lys Gly Arg Val Thr Ile Ser Val Asp Thr Ser Lys Asn Gln Phe
65                  70                  75                  80

Ser Leu Lys Ile Asn Ser Val Thr Ala Ala Asp Thr Ala Val Phe Tyr
                85                  90                  95

Cys Ala Arg Ala Ser Gly Ser His Thr Phe Asp Ile Trp Gly Gln Gly
            100                 105                 110

Thr Met Val Thr Val Ser Ser
        115

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
ggtggctcca tcaacagtgt tacttactac                                    30

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Gly Gly Ser Ile Asn Ser Val Thr Tyr Tyr
1               5                   10

<210> SEQ ID NO 55
<211> LENGTH: 21
<212> TYPE: DNA
<213> ORGANISM: Artificial Sequence
<220> FEATURE:
<223> OTHER INFORMATION: Synthetic

<400> SEQUENCE: 55
atcaaattca gtgggagcac c                                             21

<210> SEQ ID NO 56
<211> LENGTH: 7
<212> TYPE: PRT
<213> ORGANISM: Artificial Sequence
<220> FEATURE:
<223> OTHER INFORMATION: Synthetic

<400> SEQUENCE: 56

Ile Lys Phe Ser Gly Ser Thr
1               5

<210> SEQ ID NO 57

<210> SEQ ID NO 57
<211> LENGTH: 33
<212> TYPE: DNA
<213> ORGANISM: Artificial Sequence
<220> FEATURE:
<223> OTHER INFORMATION: Synthetic

<400> SEQUENCE: 57
gcgagagctt ctggaagtca tactttttgat atc    33

<210> SEQ ID NO 58
<211> LENGTH: 11
<212> TYPE: PRT
<213> ORGANISM: Artificial Sequence
<220> FEATURE:
<223> OTHER INFORMATION: Synthetic

<400> SEQUENCE: 58

Ala Arg Ala Ser Gly Ser His Thr Phe Asp Ile
 1               5                  10

<210> SEQ ID NO 59
<211> LENGTH: 324
<212> TYPE: DNA
<213> ORGANISM: Artificial Sequence
<220> FEATURE:
<223> OTHER INFORMATION: Synthetic

<400> SEQUENCE: 59
gaaacgacac tcacgcagtc tccaggcacc ctgtctttgt ctccagggga aagagccacc    60
ctctcctgca gggccagtca gagtgttagc aacagctact tagcctggta ccagcagaaa   120
cctggccagg ctcccaggct cctcatctct ggtgcgtcca gcagggtcac tggcatccca   180
gacaggttca gtggcagtgg gtctgggaca gacttcactc tcaccatcag cagactggag   240
cctgaagatt ttggaatgta ttactgtcag cagtatagta ggtcaccgat caccttcggc   300
caagggacca agctggagat caaa                                          324

<210> SEQ ID NO 60
<211> LENGTH: 108
<212> TYPE: PRT
<213> ORGANISM: Artificial Sequence
<220> FEATURE:
<223> OTHER INFORMATION: Synthetic

<400> SEQUENCE: 60

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Ser Gly Ala Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Met Tyr Tyr Cys Gln Gln Tyr Ser Arg Ser Pro
                85                  90                  95

Ile Thr Phe Gly Gln Gly Thr Lys Leu Glu Ile Lys
            100                 105

<210> SEQ ID NO 61
<211> LENGTH: 21

```
<212> TYPE: DNA
<213> ORGANISM: Artificial Sequence
<220> FEATURE:
<223> OTHER INFORMATION: Synthetic

<400> SEQUENCE: 61
cagagtgtta gcaacagcta c                                          21

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Gln Ser Val Ser Asn Ser Tyr
 1               5

<210> SEQ ID NO 63
<211> LENGTH: 9
<212> TYPE: DNA
<213> ORGANISM: Artificial Sequence
<220> FEATURE:
<223> OTHER INFORMATION: Synthetic

<400> SEQUENCE: 63 ggtgcgtcc                                                         9

<210> SEQ ID NO 64
<211> LENGTH: 3
<212> TYPE: PRT
<213> ORGANISM: Artificial Sequence
<220> FEATURE:
<223> OTHER INFORMATION: Synthetic

<400> SEQUENCE: 64

Gly Ala Ser
 1

<210> SEQ ID NO 65
<211> LENGTH: 27
<212> TYPE: DNA
<213> ORGANISM: Artificial Sequence
<220> FEATURE:
<223> OTHER INFORMATION: Synthetic

<400> SEQUENCE: 65
cagcagtata gtaggtcacc gatcacc                                    27

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Gln Gln Tyr Ser Arg Ser Pro Ile Thr
 1               5

<210> SEQ ID NO 67
<211> LENGTH: 360
<212> TYPE: DNA
<213> ORGANISM: Artificial Sequence
<220> FEATURE:
<223> OTHER INFORMATION: Synthetic
```

<400> SEQUENCE: 67

```
gaagtgcagc tggtgcagtc tgggggagcc ttggtacaac ctgggggtc cctgagactc      60
tcctgtgcag cctctggatt cacctttaac aactttgcca tgacctgggt ccgccaggct    120
ccagggaagg gcctggagtg ggtctcaact attagtggta gtggcgttga cacatactgc    180
gcagactccg tgaagggccg gttcaccatc tccagagaca attccaagaa cacactgtat    240
ctgcaaatga acagcctgag agccgaggac acggccgtat attactgttc gaaagatggc    300
gccttctata gtggctacga acactactgg ggccagggaa ccacggtcac cgtctcctca    360
```

<210> SEQ ID NO 68
<211> LENGTH: 120
<212> TYPE: PRT
<213> ORGANISM: Artificial Sequence
<220> FEATURE:
<223> OTHER INFORMATION: Synthetic

<400> SEQUENCE: 68

```
Glu Val Gln Leu Val Gln Ser Gly Gly Ala Leu Val Gln Pro Gly Gly
 1               5                  10                  15
Ser Leu Arg Leu Ser Cys Ala Ala Ser Gly Phe Thr Phe Asn Asn Phe
            20                  25                  30
Ala Met Thr Trp Val Arg Gln Ala Pro Gly Lys Gly Leu Glu Trp Val
        35                  40                  45
Ser Thr Ile Ser Gly Ser Gly Val Asp Thr Tyr Cys Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ser Lys Asp Gly Ala Phe Tyr Ser Gly Tyr Glu His Tyr Trp Gly Gln
            100                 105                 110
Gly Thr Thr Val Thr Val Ser Ser
        115                 120
```

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69

```
ggattcacct taacaacttt tgcc                                            24
```

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

```
Gly Phe Thr Phe Asn Asn Phe Ala
 1               5
```

<210> SEQ ID NO 71
<211> LENGTH: 24
<212> TYPE: DNA
<213> ORGANISM: Artificial Sequence
<220> FEATURE:
<223> OTHER INFORMATION: Synthetic

<400> SEQUENCE: 71
attagtggta gtggcgttga caca                                              24

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Ile Ser Gly Ser Gly Val Asp Thr
1               5

<210> SEQ ID NO 73
<211> LENGTH: 39
<212> TYPE: DNA
<213> ORGANISM: Artificial Sequence
<220> FEATURE:
<223> OTHER INFORMATION: Synthetic

<400> SEQUENCE: 73
tcgaaagatg gcgccttcta tagtggctac gaacactac                              39

<210> SEQ ID NO 74
<211> LENGTH: 13
<212> TYPE: PRT
<213> ORGANISM: Artificial Sequence
<220> FEATURE:
<223> OTHER INFORMATION: Synthetic

<400> SEQUENCE: 74

Ser Lys Asp Gly Ala Phe Tyr Ser Gly Tyr Glu His Tyr
1               5                   10

<210> SEQ ID NO 75
<211> LENGTH: 324
<212> TYPE: DNA
<213> ORGANISM: Artificial Sequence
<220> FEATURE:
<223> OTHER INFORMATION: Synthetic

<400> SEQUENCE: 75
gaaacgacac tcacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtacatcca acagggccac tggcatccca       180
gacaggttca gtggcagtgg gtctgggaca gacttcactc tcaccatcag cagactggag       240
tctgaagatt ttgcagtgta ttactgtcag cagtatggta gctcacctcg acgttcggc        300 caagggacca aggtggagat caaa                                             324

<210> SEQ ID NO 76
<211> LENGTH: 108
<212> TYPE: PRT
<213> ORGANISM: Artificial Sequence
<220> FEATURE:
<223> OTHER INFORMATION: Synthetic

<400> SEQUENCE: 76

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ser Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys
            100                 105

<210> SEQ ID NO 77
<211> LENGTH: 21
<212> TYPE: DNA
<213> ORGANISM: Artificial Sequence
<220> FEATURE:
<223> OTHER INFORMATION: Synthetic

<400> SEQUENCE: 77
cagagtgtta gcagcagcta c                                           21

<210> SEQ ID NO 78
<211> LENGTH: 7
<212> TYPE: PRT
<213> ORGANISM: Artificial Sequence
<220> FEATURE:
<223> OTHER INFORMATION: Synthetic

<400> SEQUENCE: 78

Gln Ser Val Ser Ser Ser Tyr
1               5

<210> SEQ ID NO 79
<211> LENGTH: 9
<212> TYPE: DNA
<213> ORGANISM: Artificial Sequence
<220> FEATURE:
<223> OTHER INFORMATION: Synthetic

<400> SEQUENCE: 79 ggtacatcc                                                          9

<210> SEQ ID NO 80
<211> LENGTH: 3
<212> TYPE: PRT
<213> ORGANISM: Artificial Sequence
<220> FEATURE:
<223> OTHER INFORMATION: Synthetic

<400> SEQUENCE: 80

Gly Thr Ser
1

<210> SEQ ID NO 81
<211> LENGTH: 27
<212> TYPE: DNA
<213> ORGANISM: Artificial Sequence
<220> FEATURE:
<223> OTHER INFORMATION: Synthetic

<400> SEQUENCE: 81
cagcagtatg gtagctcacc tcggacg                                                    27

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

Gln Gln Tyr Gly Ser Ser Pro Arg Thr
 1               5

<210> SEQ ID NO 83
<211> LENGTH: 357
<212> TYPE: DNA
<213> ORGANISM: Artificial Sequence
<220> FEATURE:
<223> OTHER INFORMATION: Synthetic

<400> SEQUENCE: 83
gaagtgcagc tggtgcagtc tggacctgag gtgaagaagc ctggggcctc agtgaaggtc    60
tcctgcaagg cttctggtta cacctttacc tactatggta tcagttggat acgacagacc   120
cctggacaag ggcttgagtg gatgggatgg atcagcgctt acgatggtaa cacagactat   180
gcacagaagt tccaagacag aatcaccatg accacagaca catcctcgac acagcctac   240 atggaactga ggagcctgag atctgacgac acggccgtct attactgtgc gaggtatagt   300
tggaacaagc actggttcga ccccctgggc cagggaacca tggtcaccgt ctcttca      357

<210> SEQ ID NO 84
<211> LENGTH: 119
<212> TYPE: PRT
<213> ORGANISM: Artificial Sequence
<220> FEATURE:
<223> OTHER INFORMATION: Synthetic

<400> SEQUENCE: 84

Glu Val Gln Leu Val Gln Ser Gly Pro Glu Val Lys Lys Pro Gly Ala
 1               5                  10                  15

Ser Val Lys Val Ser Cys Lys Ala Ser Gly Tyr Thr Phe Thr Tyr Tyr
            20                  25                  30

Gly Ile Ser Trp Ile Arg Gln Thr Pro Gly Gln Gly Leu Glu Trp Met
        35                  40                  45

Gly Trp Ile Ser Ala Tyr Asp Gly Asn Thr Asp Tyr Ala Gln Lys Phe
    50                  55                  60

Gln Asp Arg Ile Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Ser Trp Asn Lys His Trp Phe Asp Pro Trp Gly Gln Gly
            100                 105                 110

Thr Met Val Thr Val Ser Ser
        115

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
ggttacacct ttacctacta tggt                                              24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Gly Tyr Thr Phe Thr Tyr Tyr Gly
 1               5

<210> SEQ ID NO 87
<211> LENGTH: 24
<212> TYPE: DNA
<213> ORGANISM: Artificial Sequence
<220> FEATURE:
<223> OTHER INFORMATION: Synthetic

<400> SEQUENCE: 87
atcagcgctt acgatggtaa caca                                              24

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

Ile Ser Ala Tyr Asp Gly Asn Thr
 1               5

<210> SEQ ID NO 89
<211> LENGTH: 36
<212> TYPE: DNA
<213> ORGANISM: Artificial Sequence
<220> FEATURE:
<223> OTHER INFORMATION: Synthetic

<400> SEQUENCE: 89
gcgaggtata gttggaacaa gcactggttc gacccc                                 36

<210> SEQ ID NO 90
<211> LENGTH: 12
<212> TYPE: PRT
<213> ORGANISM: Artificial Sequence
<220> FEATURE:
<223> OTHER INFORMATION: Synthetic

<400> SEQUENCE: 90

Ala Arg Tyr Ser Trp Asn Lys His Trp Phe Asp Pro
 1               5                  10

<210> SEQ ID NO 91
<211> LENGTH: 324
<212> TYPE: DNA
<213> ORGANISM: Artificial Sequence
<220> FEATURE:
<223> OTHER INFORMATION: Synthetic

<400> SEQUENCE: 91
gaaattgtga tgacacagtc tccaggcacc ctgtctttgt ctccagggga cagagccacc       60

```
ctctcctgca gggccagtca gagtgttacc ggcagctact tagcctggta ccagcagaaa    120
cctggccagg ctcccagact cctcatctat ggtgcatcca acagggccac tggcatccca    180
gacaggttca ctggcagtgg gtctgggaca gacttcactc tcaccatcag cagactggag    240
cctgaagatt ttgcagtgta tttctgtcaa cagtctgctt tctcaccgtg acgttcggc     300 caggggacca aggtggaaat caaa                                           324
```

<210> SEQ ID NO 92
<211> LENGTH: 108
<212> TYPE: PRT
<213> ORGANISM: Artificial Sequence
<220> FEATURE:
<223> OTHER INFORMATION: Synthetic

<400> SEQUENCE: 92

```
Glu Ile Val Met Thr Gln Ser Pro Gly Thr Leu Ser Leu Ser Pro Gly
 1               5                  10                  15

Asp Arg Ala Thr Leu Ser Cys Arg Ala Ser Gln Ser Val Thr Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Thr
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Phe Cys Gln Gln Ser Ala Phe Ser Pro
                85                  90                  95

Trp Thr Phe Gly Gln Gly Thr Lys Val Glu Ile Lys
            100                 105
```

<210> SEQ ID NO 93
<211> LENGTH: 21
<212> TYPE: DNA
<213> ORGANISM: Artificial Sequence
<220> FEATURE:
<223> OTHER INFORMATION: Synthetic

<400> SEQUENCE: 93

```
cagagtgtta ccggcagcta c                                              21
```

<210> SEQ ID NO 94
<211> LENGTH: 7
<212> TYPE: PRT
<213> ORGANISM: Artificial Sequence
<220> FEATURE:
<223> OTHER INFORMATION: Synthetic

<400> SEQUENCE: 94

```
Gln Ser Val Thr Gly Ser Tyr
 1               5
```

<210> SEQ ID NO 95
<211> LENGTH: 9
<212> TYPE: DNA
<213> ORGANISM: Artificial Sequence
<220> FEATURE:
<223> OTHER INFORMATION: Synthetic

<400> SEQUENCE: 95

```
ggtgcatcc                                                             9
```

-continued

```
<210> SEQ ID NO 96
<211> LENGTH: 3
<212> TYPE: PRT
<213> ORGANISM: Artificial Sequence
<220> FEATURE:
<223> OTHER INFORMATION: Synthetic

<400> SEQUENCE: 96

Gly Ala Ser
 1

<210> SEQ ID NO 97
<211> LENGTH: 27
<212> TYPE: DNA
<213> ORGANISM: Artificial Sequence
<220> FEATURE:
<223> OTHER INFORMATION: Synthetic

<400> SEQUENCE: 97
caacagtctg ctttctcacc gtggacg                                         27

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Gln Gln Ser Ala Phe Ser Pro Trp Thr
 1               5

<210> SEQ ID NO 99
<211> LENGTH: 363
<212> TYPE: DNA
<213> ORGANISM: Artificial Sequence
<220> FEATURE:
<223> OTHER INFORMATION: Synthetic

<400> SEQUENCE: 99
caggtgcagc tgcaggagtc gggcccagga ctggtgaagc cttcacagac cctgtccctc     60
acctgcactg tctctggtgg ctccatcagc agtggtggtt actactggag ttggatccgc    120
cagcacccag ggaagggcct ggagtggatt gggtacatcc attatagtgg aacacccac    180 tacaatccga ccctcaagag tcgaattacc atatcagtag acacgtctaa gaaccagttc    240
tcccttgagg tgaactctgt gactgccgcg gacacggccg tatactactg tgcgaggaat    300
atggttcggg gagttcactg gttcgacccc tggggccagg gaaccacggt caccgtctcc    360
tca                                                                  363

<210> SEQ ID NO 100
<211> LENGTH: 121
<212> TYPE: PRT
<213> ORGANISM: Artificial Sequence
<220> FEATURE:
<223> OTHER INFORMATION: Synthetic

<400> SEQUENCE: 100

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
             20                  25                  30

Gly Tyr Tyr Trp Ser Trp Ile Arg Gln His Pro Gly Lys Gly Leu Glu
         35                  40                  45
```

Trp Ile Gly Tyr Ile His Tyr Ser Gly Asn Thr His Tyr Asn Pro Thr
            50                  55                  60

Leu Lys Ser Arg Ile Thr Ile Ser Val Asp Thr Ser Lys Asn Gln Phe
 65                  70                  75                  80

Ser Leu Glu Val Asn Ser Val Thr Ala Ala Asp Thr Ala Val Tyr Tyr
                85                  90                  95

Cys Ala Arg Asn Met Val Arg Gly Val His Trp Phe Asp Pro Trp Gly
            100                 105                 110

Gln Gly Thr Thr Val Thr Val Ser Ser
        115                 120

<210> SEQ ID NO 101
<211> LENGTH: 30
<212> TYPE: DNA
<213> ORGANISM: Artificial Sequence
<220> FEATURE:
<223> OTHER INFORMATION: Synthetic

<400> SEQUENCE: 101
ggtggctcca tcagcagtgg tggttactac                                       30

<210> SEQ ID NO 102
<211> LENGTH: 10
<212> TYPE: PRT
<213> ORGANISM: Artificial Sequence
<220> FEATURE:
<223> OTHER INFORMATION: Synthetic

<400> SEQUENCE: 102

Gly Gly Ser Ile Ser Ser Gly Gly Tyr Tyr
 1               5                  10

<210> SEQ ID NO 103
<211> LENGTH: 21
<212> TYPE: DNA
<213> ORGANISM: Artificial Sequence
<220> FEATURE:
<223> OTHER INFORMATION: Synthetic

<400> SEQUENCE: 103
atccattata gtgggaacac c                                                21

<210> SEQ ID NO 104
<211> LENGTH: 7
<212> TYPE: PRT
<213> ORGANISM: Artificial Sequence
<220> FEATURE:
<223> OTHER INFORMATION: Synthetic

<400> SEQUENCE: 104

Ile His Tyr Ser Gly Asn Thr
 1               5

<210> SEQ ID NO 105
<211> LENGTH: 39
<212> TYPE: DNA
<213> ORGANISM: Artificial Sequence
<220> FEATURE:
<223> OTHER INFORMATION: Synthetic

<400> SEQUENCE: 105
gcgaggaata tggttcgggg agttcactgg ttcgacccc                             39

<210> SEQ ID NO 106
<211> LENGTH: 13
<212> TYPE: PRT
<213> ORGANISM: Artificial Sequence
<220> FEATURE:
<223> OTHER INFORMATION: Synthetic

<400> SEQUENCE: 106

Ala Arg Asn Met Val Arg Gly Val His Trp Phe Asp Pro
 1               5                  10

<210> SEQ ID NO 107
<211> LENGTH: 324
<212> TYPE: DNA
<213> ORGANISM: Artificial Sequence
<220> FEATURE:
<223> OTHER INFORMATION: Synthetic

<400> SEQUENCE: 107
gaaatagtgt tgacacagtc tccaggcacc ctgtctttgt ctccagggga gagagccacc    60
ctcttctgtt gggccagtcg gagtgttagc agcagctact tagcctggta ccagcagaaa   120
cctggccagg ctcccaggct cctcatctct ggtgcatcca gcagggccac tggcatccca   180
gacaggttca gtggcagtgg gtctgggaca gacttcactc tcaccatcag cagactggag   240
cctgaagatt ttgcagtata tttctgtcaa cagtatagta gttcaccgct cactttcggc   300
ggagggacca agctggagat caaa                                          324

<210> SEQ ID NO 108
<211> LENGTH: 108
<212> TYPE: PRT
<213> ORGANISM: Artificial Sequence
<220> FEATURE:
<223> OTHER INFORMATION: Synthetic

<400> SEQUENCE: 108

Glu Ile Val Leu Thr Gln Ser Pro Gly Thr Leu Ser Leu Ser Pro Gly
 1               5                  10                  15

Glu Arg Ala Thr Leu Phe Cys Trp Ala Ser Arg Ser Val Ser Ser Ser
             20                  25                  30

Tyr Leu Ala Trp Tyr Gln Gln Lys Pro Gly Gln Ala Pro Arg Leu Leu
         35                  40                  45

Ile Ser Gly Ala Ser Ser Arg Ala Thr Gly Ile Pro Asp Arg Phe Ser
     50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Ser Ser Ser Pro
                 85                  90                  95

Leu Thr Phe Gly Gly Gly Thr Lys Leu Glu Ile Lys
            100                 105

<210> SEQ ID NO 109
<211> LENGTH: 21
<212> TYPE: DNA
<213> ORGANISM: Artificial Sequence
<220> FEATURE:
<223> OTHER INFORMATION: Synthetic

<400> SEQUENCE: 109
cggagtgtta gcagcagcta c                                              21

<210> SEQ ID NO 110

```
<211> LENGTH: 7
<212> TYPE: PRT
<213> ORGANISM: Artificial Sequence
<220> FEATURE:
<223> OTHER INFORMATION: Synthetic

<400> SEQUENCE: 110

Arg Ser Val Ser Ser Ser Tyr
 1               5

<210> SEQ ID NO 111
<211> LENGTH: 9
<212> TYPE: DNA
<213> ORGANISM: Artificial Sequence
<220> FEATURE:
<223> OTHER INFORMATION: Synthetic

<400> SEQUENCE: 111 ggtgcatcc                                                                9

<210> SEQ ID NO 112
<211> LENGTH: 3
<212> TYPE: PRT
<213> ORGANISM: Artificial Sequence
<220> FEATURE:
<223> OTHER INFORMATION: Synthetic

<400> SEQUENCE: 112

Gly Ala Ser
 1

<210> SEQ ID NO 113
<211> LENGTH: 27
<212> TYPE: DNA
<213> ORGANISM: Artificial Sequence
<220> FEATURE:
<223> OTHER INFORMATION: Synthetic

<400> SEQUENCE: 113
caacagtata gtagttcacc gctcact                                           27

<210> SEQ ID NO 114
<211> LENGTH: 9
<212> TYPE: PRT
<213> ORGANISM: Artificial Sequence
<220> FEATURE:
<223> OTHER INFORMATION: Synthetic

<400> SEQUENCE: 114

Gln Gln Tyr Ser Ser Ser Pro Leu Thr
 1               5

<210> SEQ ID NO 115
<211> LENGTH: 369
<212> TYPE: DNA
<213> ORGANISM: Artificial Sequence
<220> FEATURE:
<223> OTHER INFORMATION: Synthetic

<400> SEQUENCE: 115
caggtgcagc tggtggagtc tgggggaggc gtggtccagc ctggggaggtc cctgagactc      60 tcctgtgcag cgtctggatt caccttcagt agttatggca tgcactgggt ccgccaggct     120
ccaggcaagg ggctggagtg ggtgtcattt ttatggtatg atggaactaa taaaaactat     180
gtagagtccg tgaagggccg attcaccatc tcaagagaca attccaagaa tatgctgtat     240
```

```
ctggaaatga acagcctgag agccgaggac acggctgtgt attactgtgc gagagatcac    300
gattttagga gtggttatga ggggtggttc gaccccgggg gccagggaac cctggtcacc    360
gtctcctca                                                           369
```

<210> SEQ ID NO 116
<211> LENGTH: 123
<212> TYPE: PRT
<213> ORGANISM: Artificial Sequence
<220> FEATURE:
<223> OTHER INFORMATION: Synthetic

<400> SEQUENCE: 116

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Phe Leu Trp Tyr Asp Gly Thr Asn Lys Asn Tyr Val Glu Ser Val
     50                  55                  60

Lys Gly Arg Phe Thr Ile Ser Arg Asp Asn Ser Lys Asn Met Leu Tyr
 65                  70                  75                  80

Leu Glu Met Asn Ser Leu Arg Ala Glu Asp Thr Ala Val Tyr Tyr Cys
                 85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120
```

<210> SEQ ID NO 117
<211> LENGTH: 321
<212> TYPE: DNA
<213> ORGANISM: Artificial Sequence
<220> FEATURE:
<223> OTHER INFORMATION: Synthetic

<400> SEQUENCE: 117

```
gaaatagtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcaacac cgtagcaact ggcctccac tttcggcgga   300 gggaccaagg tggaaatcaa a                                            321
```

<210> SEQ ID NO 118
<211> LENGTH: 107
<212> TYPE: PRT
<213> ORGANISM: Artificial Sequence
<220> FEATURE:
<223> OTHER INFORMATION: Synthetic

<400> SEQUENCE: 118

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
```

```
                35                      40                      45
Tyr Asp Ala Ser Asn Arg Ala Thr Gly Ile Pro Ala Arg Phe Ser Gly
        50                      55                      60

Ser Gly Ser Gly Thr Asp Phe Thr Leu Thr Ile Ser Ser Leu Glu Pro
65                      70                      75                      80

Glu Asp Phe Ala Val Tyr Tyr Cys Gln His Arg Ser Asn Trp Pro Pro
                85                      90                      95

Thr Phe Gly Gly Gly Thr Lys Val Glu Ile Lys
            100                     105
```